US009814572B2

(12) United States Patent
Edelman et al.

(10) Patent No.: US 9,814,572 B2
(45) Date of Patent: Nov. 14, 2017

(54) PROSTHETIC HEART VALVE FORMATION

(71) Applicant: Boston Scientific SciMed, Inc., Maple Grove, MN (US)

(72) Inventors: Peter G. Edelman, Maple Grove, MN (US); Horng-Ban Lin, Maple Grove, MN (US); Scott Fisher, Solon, OH (US); Jeffrey S. Lindquist, Maple Grove, MN (US); Huisun Wang, Maple Grove, MN (US); Richard C. Gunderson, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/656,044

(22) Filed: Mar. 12, 2015

(65) Prior Publication Data
US 2015/0182332 A1    Jul. 2, 2015

Related U.S. Application Data

(62) Division of application No. 13/932,968, filed on Jul. 1, 2013, now Pat. No. 9,056,006.
(Continued)

(51) Int. Cl.
*A61F 2/24* (2006.01)
*A61L 27/18* (2006.01)
(Continued)

(52) U.S. Cl.
CPC .............. *A61F 2/2412* (2013.01); *A61F 2/24* (2013.01); *A61F 2/2415* (2013.01);
(Continued)

(58) Field of Classification Search
CPC ........................................................ A61F 2/24
See application file for complete search history.

(56) References Cited

U.S. PATENT DOCUMENTS 4,340,091 A    7/1982   Robert et al.
4,753,652 A    6/1988   Langer et al.
(Continued)

FOREIGN PATENT DOCUMENTS

WO    WO 02/24119           3/2002
WO    WO 0224119 A1  *  3/2002   ........... A61F 2/2412
(Continued)

OTHER PUBLICATIONS

Bates et al., "Multiblock Polymers: Panacea or Pandora's Box?," *Science*, 2012, 336:434-440.
(Continued)

*Primary Examiner* — Jacqueline Woznicki
(74) *Attorney, Agent, or Firm* — Pauly, DeVries Smith & Deffner LLC

(57) ABSTRACT

A prosthetic heart valve includes a base and a plurality of polymeric leaflets. Each leaflet has a root portion coupled to the base, and each leaflet has an edge portion substantially opposite the root portion and movable relative to the root portion to coapt with a respective edge portion of at least one of the other leaflets of the plurality of leaflets. Each leaflet includes) at least two polymers along at least one portion of the leaflet, and each leaflet has a composition gradient of each of the at least two polymers along at least one portion of the leaflet.

16 Claims, 21 Drawing Sheets

Related U.S. Application Data

(60) Provisional application No. 61/667,267, filed on Jul. 2, 2012.

(51) Int. Cl.

| | | |
|---|---|---|
| *A61L 27/34* | (2006.01) | |
| *B05D 7/22* | (2006.01) | |
| *B05B 7/04* | (2006.01) | |
| *B05B 12/00* | (2006.01) | |
| *B05B 13/02* | (2006.01) | |
| *B05B 13/06* | (2006.01) | |
| *B05B 12/14* | (2006.01) | |
| *B33Y 80/00* | (2015.01) | |
| *B05D 1/02* | (2006.01) | |

(52) U.S. Cl.
CPC ............ *A61F 2/2418* (2013.01); *A61L 27/18* (2013.01); *A61L 27/34* (2013.01); *B05B 7/0408* (2013.01); *B05B 7/0416* (2013.01); *B05B 7/0433* (2013.01); *B05B 7/0466* (2013.01); *B05B 12/00* (2013.01); *B05B 12/1454* (2013.01); *B05B 13/0207* (2013.01); *B05B 13/0627* (2013.01); *B05D 7/222* (2013.01); *A61F 2210/0076* (2013.01); *A61F 2250/0014* (2013.01); *A61F 2250/0018* (2013.01); *A61F 2250/0028* (2013.01); *A61F 2250/0036* (2013.01); *A61F 2250/0037* (2013.01); *A61L 2430/20* (2013.01); *B05D 1/02* (2013.01); *B05D 2254/02* (2013.01); *B33Y 80/00* (2014.12); *Y10T 29/49405* (2015.01)

(56) References Cited

U.S. PATENT DOCUMENTS

| | | |
|---|---|---|
| 5,740,051 A | 4/1998 | Sanders, Jr. et al. |
| 6,165,215 A | 12/2000 | Rottenberg et al. |
| 7,335,264 B2 | 2/2008 | Motherwell et al. |
| 7,521,296 B2 | 4/2009 | Wood et al. |
| 7,615,335 B2 | 11/2009 | Barr et al. |
| 7,786,670 B2 | 8/2010 | Veres et al. |
| 7,988,900 B2 | 8/2011 | Beith |
| 8,324,290 B2 | 12/2012 | Desai et al. |
| 8,590,747 B2 | 11/2013 | Keller et al. |
| 8,845,580 B2 | 9/2014 | Gellman et al. |
| 9,056,006 B2 | 6/2015 | Edelman et al. |
| 9,554,900 B2 | 1/2017 | Bruchman et al. |
| 2001/0025196 A1 | 9/2001 | Chinn |
| 2002/0082689 A1 | 6/2002 | Chinn |
| 2003/0055496 A1* | 3/2003 | Cai .................. A61F 2/2412 623/2.19 |
| 2003/0078652 A1 | 4/2003 | Sutherland |
| 2003/0097175 A1 | 5/2003 | O'Connor et al. |
| 2003/0171802 A1 | 9/2003 | Wilder et al. |
| 2003/0183982 A1 | 10/2003 | Jansen et al. |
| 2004/0015233 A1 | 1/2004 | Jansen |
| 2005/0228486 A1 | 10/2005 | Flagle et al. |
| 2006/0190074 A1 | 8/2006 | Hill et al. |
| 2007/0118210 A1* | 5/2007 | Pinchuk ............ A61F 2/2412 623/1.26 |
| 2007/0144124 A1 | 6/2007 | Schewe et al. |
| 2008/0045420 A1 | 2/2008 | Karagianni et al. |
| 2010/0023104 A1* | 1/2010 | Desai .................. A61L 27/18 607/119 |
| 2010/0179298 A1 | 7/2010 | Faust et al. |
| 2011/0208299 A1 | 8/2011 | Marissen |
| 2013/0150957 A1 | 6/2013 | Weber et al. |
| 2013/0211508 A1* | 8/2013 | Lane .................. A61F 2/2403 623/2.11 |
| 2014/0005771 A1* | 1/2014 | Braido ................ A61F 2/2412 623/2.12 |
| 2014/0005772 A1 | 1/2014 | Edelman et al. |
| 2014/0018440 A1 | 1/2014 | Boden et al. |
| 2014/0163671 A1 | 6/2014 | Bruchman et al. |
| 2014/0180402 A1 | 6/2014 | Bruchman et al. |
| 2016/0296322 A1 | 10/2016 | Edelman |
| 2016/0296323 A1 | 10/2016 | Wulfman et al. |
| 2016/0296325 A1 | 10/2016 | Edelman |
| 2017/0000610 A1 | 1/2017 | Eppihimer et al. |
| 2017/0014227 A1 | 1/2017 | Boden et al. |
| 2017/0071729 A1 | 3/2017 | Wrobel |

FOREIGN PATENT DOCUMENTS

| | | |
|---|---|---|
| WO | 02074201 | 9/2002 |
| WO | 2006000763 | 1/2006 |
| WO | 2008097592 | 8/2008 |
| WO | 2009038761 | 3/2009 |
| WO | 2010020660 | 2/2010 |
| WO | 2010048281 | 4/2010 |
| WO | 2014008207 | 1/2014 |
| WO | 2014149319 | 9/2014 |
| WO | 2016164197 | 10/2016 |
| WO | 2016164209 | 10/2016 |
| WO | 2017004035 | 1/2017 |
| WO | 2017011392 | 1/2017 |
| WO | 2017048575 | 3/2017 |

OTHER PUBLICATIONS

Glycosaminoglycan, Wikipedia, posted on or before Oct. 16, 2004, retrieved Feb. 13, 2014, http://en.wikipedia.org/wiki/Glycosaminoglycan, 6 pages.

International Search Report and Written Opinion in International Application No. PCT/US2013/048976, dated Nov. 19, 2013, 20 pages.

Liu et al., "Effect of fiber orientation on the stress distribution within a leaflet of a polymer composite heart valve in the closed position," *J of Biomedichanics*, 2007, 40:1099-1106.

Wang et al., "In-Vivo Assessment of a Novel Polymer (SIBS) Trileaflet Heart Valve," *J Heart Valve Dis*, Jul. 2010, 19(4):499-505.

Wheatley et al., "Polyurethane: material for the next generation of heart valve prostheses?," *Eur J Cardio-Thoracic Surg*, 2000, 17:440-448.

Zhang et al., Eur. Polym. J. vol. 34, No. 3-4, pp. 571-575 (1998).

International Preliminary Report on Patentability in International Application No. PCT/US2013/048976, dated Jan. 6, 2015, 10 pages.

"First Office Action," for Chinese Patent Application No. 201380044842.0 dated Dec. 18, 2015 (15 pages) with English Translation.

Athappan, Ganesh et al., "Influence of Transcatheter Aortic Valve Replacement Strategy and Valve Design on Stroke After Transcatheter Aortic Valve Replacement: A Meta-Analysis and Systematic Review of Literature," J Am Coll Cardiol. 2014;63 (20):2101-2110 (10 pages).

Généreux, Philippe et al., "Vascular Complications After Transcatheter Aortic Valve Replacement: Insights from the PART-NER Trial," J Am Coll Cardiol. 2012; 60(12):1043-1052 (10 pages).

Kang, Jungmee et al., "Polyisobutylene-Based Polyurethanes with Unprecedented Properties and How They Came About," Journal of Polymer Science Part A: Polymer Chemistry, 2011. 49(18): p. 3891-3904 (14 pages).

"Liquid-Crystal Polymer," Wikipedia, the Free Encyclopedia <http://en/wikipedia.org/wiki/Liquid-crystal_polymer>, retrieved Jun. 2, 2016 (3 pages).

Schneider, Tobias et al., "Influence of fiber orientation in electrospun polymer scaffolds on viability, adhesion and differentiation of articular chondrocytes," Clinical Hemorheology and Microcirculation 52 (2012) 325-336 (13 pages).

Yao, Jian et al., "High Strength and High Modulus Electrospun Nanofibers," Fibers 2014; 2:158-187 (30 pages).

Aksoy, Ayse E. et al., "Surface Modification of Polyurethanes with Covalent Immobilization of Heparin," Macromolecular Symposia, vol. 269, Issue 1, pp. 145-153, Aug. 2008 (9 pages).

(56) References Cited

OTHER PUBLICATIONS

Alferiev, Ivan et al., "Prevention of polyurethane valve cusp calcification with covalently attached bisphosphonate diethylamino moieties," J Biomed Mater Res 66A: 385-395, 2003 (11 pages).

Barkoula, Nektaria-Marianthi et al., "Processing of Single Polymer Composites Using the Concept of Constrained Fibers," Polymer Composites, 2005, 26: p. 114-120 (7 pages).

Bastiaansen, Cees W. et al., "Melting Behavior of Gelspun-Drawn Polyolefins," Makromol. Chem., Macromol. Symp., 1989. 28: p. 73-84 (12 pages).

Bernacca, Gillian M. et al., "Mechanical and morphological study of biostable polyurethane heart valve leaflets explanted from sheep," J Biomed Mater Res 61:138-145, 2002 (8 pages).

Bhattacharyya, D. et al., "Polyamide 6 single polymer composites," eXPRESS Polym. Lett., 2009. 3(8): p. 525-532 (8 pages).

Cacciola, G. et al., "A Synthetic Fiber-Reinforced Stentless Heart Valve," Journal of Biomechanics, Jan. 1, 2000, pp. 653-658, XP055284947, Retrieved from the Internet: URL:http://ac.els-cdn.com.

Cacciola, G. et al., "A Three-Dimesional Mechanical Analysis of a Stentless Fibre-Reinforced Aortic Valve Prosthesis," Journal of Biomechanics, Jan. 1, 2000, pp. 521-530, XP055284955, Retrieved from the Internet: URL:http://ac.els-cdn.com.

Charles, Lyndon F. et al., "Self-reinforced composites of hydroxyapatite-coated PLLA fibers: fabrication and mechanical characterization," J. Mech. Behav. Biomed. Mater., 2013. 17: p. 269-277 (9 pages).

Claiborne, Thomas E. et al., "In Vitro Evaluation of a Novel Hemodynamically Optimized Trileaflet Polymeric Prosthetic Heart Valve," Journal of Biomechanical Engineering 2013, vol. 135 (8 pages).

"Communication Pursuant to Article 94(3) EPC," for European Patent Application No. 13739321.1 dated Sep. 8, 2016 (4 pages).

De Yoreo, James J. et al., "Principles of Crystal Nucleation and Growth," Biomineralization, Mineral Soc. Am., Washington, DC, 2003, pp. 57-93 (37 pages).

Dencheva, Nadya et al., "Structure-properties relationship in single polymer composites based on polyamide 6 prepared by in-mold anionic polymerization," J. Mater. Sci., 2013. 48(20): p. 7260-7273 (14 pages).

Duhovic, Miro P. et al., "Polyamide 66 polymorphic single polymer composites," Open Macromol. J., 2009. 3: p. 37-40. (4 pages).

Fakirov, Stoyko "Nano- and Microfibrillar Single-Polymer Composites: A Review," Macromol. Mater. Eng., 2013. 298(1): p. 9-32 (24 pages).

Feng, Yakai et al., "Surface modification of polycarbonate urethane by covalent linkage of heparin with a PEG spacer," Transactions of Tianjin University, Feb. 2013, vol. 19, Issue 1, pp. 58-65 (8 pages).

Gallocher, "Durability Assessment of Polymer Trileaflet Heart Valves," FIU Electronic Theses and Dissertations, Paper 54, 2007 (237 pages).

Gong, Ying et al., "Polyamide single polymer composites prepared via in situ anionic polymerization of ε-caprolactam," Composites, Part A, 2010. 41A(8): p. 1006-1011 (6 pages).

Gong, Ying et al., "Single polymer composites by partially melting recycled polyamide 6 fibers: preparation and characterization," J. Appl. Polym. Sci., 2010. 118(6): p. 3357-3363 (7 pages).

Goyal, R. K. et al., "High performance polymer composites on PEEK reinforced with aluminum oxide," J. Appl. Polym. Sci., 2006. 100(6): p. 4623-4631 (9 pages).

Han, Dong K. et al., "In vivo biostability and calcification-resistance of surface-modified PU-PEO-SO3," Journal of Biomedical Materials Research, vol. 27, 1063-1073, 1993 (11 pages).

Hine, P.J. et al., "High stiffness and high impact strength polymer composites by hot compaction of oriented fibers and tapes," in Mechanical Properties of Polymers Based on Nanostructure and Morphology, CRC Press, 2005 (45 pages).

Hine, P.J. et al., "Hot compaction of woven nylon 6,6 multifilaments," J. Appl. Polym. Sci., 2006. 101(2): p. 991-997 (7 pages).

Hine, P.J. et al., "Hot Compaction of Woven Poly(ethylene terephthalate) Multifilaments," J. Appl. Polym. Sci., 2004. 91(4): p. 2223-2233 (11 pages).

Hine, P.J. et al., "Hybrid carbon fibre/nylon 12 single polymer composites," Composites Part A: Applied Science and Manufacturing 65 (2014) (17 pages).

"International Search Report and Written Opinion," for PCT Application No. PCT/US2016/041757 dated Oct. 12, 2016 (12 pages).

"International Search Report and Written Opinion," for PCT/US2016/024614 dated Jul. 12, 2016 (13 pages).

"International Search Report and Written Opinion," for PCT/US2016/024753 dated Jul. 22, 2016 (11 pages).

"International Search Report and Written Opinion," for PCT/US2016/039808 dated Sep. 26, 2016 (11 pages).

Jiang, Shaoyi et al., "Ultralow-Fouling, Functionalizable, and Hydrolyzable Zwitterionic Materials and Their Derivatives for Biological Applications," Adv Mater. Mar. 5, 2010;22(9):920-32 (13 pages).

Kalejs, et al., "St. Jude Epic Heart Valve Bioprostheses Versus Native Human and Porcine Aortic Valves—Comparison of Mechanical Properties," Interactive Cardiovascular and Thoracic Surgery 8 (2009) 553-557.

Kalfon-Cohen, Estelle et al., "Microstructure and nematic transition in thermotropic liquid crystalline fibers and their single polymer composites," Polym. Adv. Technol., 2007. 18(9): p. 771-779 (9 pages).

Khondker, O.A. et al., "Fabrication and mechanical properties of aramid/nylon plain knitted composites," Composites Part A: Applied Science and Manufacturing, 2004. 35(10): p. 1195-1205 (11 pages).

Kim, Nam K. et al., "Nanofibrillar Poly(vinylidene fluoride): Preparation and Functional Properties," Int. J. Polym. Mater. Polym. Biomater., 2014. 63(1): p. 23-32 (10 pages).

Kim, Nam K. et al., "Polymer-Polymer and Single Polymer Composites Involving Nanofibrillar Poly(vinylidene Fluoride): Manufacturing and Mechanical Properties," J. Macromol. Sci., Part B: Phys., 2014. 53(7): p. 1168-1181 (14 pages).

Kuang, Jinghao et al., "Universal Surface-initiated Polymerization of Antifouling Zwitterionic Brushes Using a Mussel Mimetic Peptide Initiator," Langmuir. May 8, 2012; 28(18): 7258-7266 (20 pages).

Maity, J. et al., "Homocomposites of chopped fluorinated polyethylene fiber with low-density polyethylene matrix," Mater. Sci. Eng., A, 2008. A479(1-2): p. 125-135 (11 pages).

Masoumi, et al., "Trilayered Elastomeric Scaffolds for Engineering Heart Valve Leaflets," Biomaterials. Sep. 2014; 35(27):7774-7785.

Matabola, K. P. et al., "Single polymer composites: a review," Journal of Materials Science, 2009. 44(23): p. 6213-6222 (10 pages).

Medeiros Araujo, Thiago et al., "Liquid crystalline single-polymer short-fibers composites," Composite Interfaces, 2013. 20(4): p. 287-298 (12 pages).

Ohri, Rachit et al., "Hyaluronic acid grafting mitigates calcification of glutaraldehyde-fixed bovine pericardium," J Biomed Mater Res 70A: 328-334, 2004 (7 pages).

"Second Office Action," for Chinese Patent Application No. 201380044842.0, dated Aug. 12, 2016 (16 pages) with summary.

Sun, Xiaoli et al., "α and β Interfacial Structures of the iPP/PET Matrix/Fiber Systems," Macromolecules, 2007. 40(23): p. 8244-8249 (6 pages).

Tu, Qin et al., "Synthesis of polyethylene glycol- and sulfobetaine-conjugated zwitterionic poly(l-lactide) and assay of its antifouling properties," Colloids and Surfaces B; Biointerfaces 102 (2013) 331-340 (10 pages).

Vesely, et al., "Micromechanics of the Fibrosa and the Ventricularis in Aortic Valve Leaflets," J Biomech. 1992 25(1):101-113.

Vick, Linda W. et al., "Hot compaction and consolidation of polycarbonate powder," Polym. Eng. Sci., 1998. 38(11): p. 1824-1837 (14 pages).

Wang, Qiang et al., "A novel small animal model for biocompatibility assessment of polymeric materials for use in prosthetic heart valves," J Biomed Mater Res 93A: 442-453, 2010 (12 pages).

(56) References Cited

OTHER PUBLICATIONS

Ward, I.M. et al., "Developments in oriented polymers," Plastics, Rubber and Composites, 2004. 33(5): p. 189-194 (6 pages).
Ward, I.M. et al., "Novel composites by hot compaction of fibers," Polym. Eng. Sci., 1997. 37(11): p. 1809-1814 (6 pages).
Yang, Mingjing et al., "Assessing the Resistance to Calcification of Polyurethane Membranes Used in the Manufacture of Ventricles for a Totally Implantable Artificial Heart," J Biomed Mater Res (Appl Biomater) 48: 648-659, 1999 (12 pages).
Yeh, Shiou-Bang et al., "Modification of Silicone Elastomer with Zwitterionic Silane for Durable Antifouling Properties," Langmuir 2014, 30, 11386-11393 (8 pages).
Zhang, Zhiping et al., "Effect of Crosslinking and Grafting by 60Co-γ-ray Irradiation on Carbon Black/Polyethylene Switching Materials and Fluoride Resin System in self-regulating Heating Cables," JAERI-Conf, 2000. 2000-001(JCBSRC '99, the 8th Japan-China Bilateral Symposium on Radiation Chemistry, 1999): p. 202-210 (9 pages).
Zhao, Zeng Hua et al., "Research development of single polymer composite preparation," Gongcheng Suliao Yingyong, 2010. 38(2): p. 81-84, with machine translation (11 pages).
"International Search Report and Written Opinion," for PCT application No. PCT/US2016/050691 dated Dec. 19, 2016 (14 pages).
"Response to Communication Pursuant to Article 94(3) EPC," for European Patent Application No. 13739321.1 filed with the EPO Jan. 2, 2017 (37 pages).
"Decision of Final Rejection," for China Patent Application No. 201380044842.0, dated Apr. 7, 2017 (18 pages) with Summary.

\* cited by examiner

FIG. 4A ·····{MDI-(BD-MDI)$_x$}$_y$-PTMO$_y$·····

PROSTHETIC HEART VALVE FORMATION

CROSS-REFERENCE TO RELATED APPLICATION

This application is a divisional and claims priority to application Ser. No. 13/932,968 filed on Jul. 1, 2013, which claims priority under 35 USC §119(e) to U.S. Provisional Patent Application Ser. No. 61/667,267, filed on Jul. 2, 2012, the entire contents of which is hereby incorporated by reference.

TECHNICAL FIELD

The following disclosure relates to replacement heart valves and, more particularly, to replacement heart valves including polymer leaflets.

BACKGROUND

Heart valve replacement is a widely used procedure in the treatment of structural heart disease. For example, heart valve replacement may be indicated when there is a narrowing of the native heart valve, commonly referred to as stenosis, or when the native valve leaks or regurgitates. Prosthetic heart valves used to replace these diseased valves include mechanical and tissue-based valves.

Tissue-based valves include leaflets made from biological tissue such as bovine pericardium or porcine pericardium. For use as valve leaflets, such xenograft tissues typically need to be fixed, usually by glutaraldehyde, and attached to a scaffold, usually by a suture. These processes can be labor intensive and time consuming and, given their manual nature, can be the source of some variability in valve performance.

SUMMARY

A prosthetic heart valve replaces the function of a native heart valve such that the prosthetic valve regulates the flow of blood through the heart.

In one aspect, a prosthetic heart valve includes a base and a plurality of polymeric leaflets. Each leaflet has a root portion coupled to the base, and each leaflet has an edge portion substantially opposite the root portion and movable relative to the root portion to coapt with a respective edge portion of at least one of the other leaflets of the plurality of leaflets. Each leaflet includes two or more polymers, and each leaflet has a composition gradient of each of the at least two polymers along at least one portion of the leaflet.

In some implementations, each leaflet has a substantially uniform thickness. In certain implementations, each leaflet has a decreasing thickness in a direction extending generally from the root portion to the edge portion.

In some implementations, one of the at least two polymers is a first layer, another of the at least two polymers is a second layer, and each of the layers extends in a direction generally from the root portion to the edge portion. The thickness of one or more of the first and second layers can decrease in the direction generally from the root portion to the edge portion.

In some implementations, the polymeric leaflet has a layer structure with an interior layer disposed between external layers and having a composition different from the composition of each of the external layers. Each of the external layers can have a higher hard segment-to-soft segment ratio compared to the interior layer to reduce, for example, the likelihood of tack (auto adhesion) between coapting leaflets.

In some implementations, the external layer facing the aorta is different from the external layer facing the ventricles.

In certain implementations, the composition gradient is a substantially continuous increase in the ratio of one of the at least two polymers to another one of the at least two polymers along the at least one portion of the leaflet. In some implementations, the composition gradient is a pattern of the at least two polymers along the at least one portion of the leaflet. Additionally or alternatively, each leaflet has a stiffness gradient along the at least one portion of the leaflet corresponding to the composition gradient. For example, each leaflet can have a composition gradient and a stiffness gradient in a direction extending from the root portion to the edge portion and/or in a direction extending along a thickness of the leaflet. In certain implementations, each leaflet has a maximum thickness of 100 µm or less.

In some implementations, each of the at least two polymers has respective hard segments and soft segments and the ratio of hard segments to soft segments in one of the at least two polymers is higher than the ratio of hard segments to soft segments in another one of the at least two polymers. For example, each of the at least two polymers can be a respective block polymer (e.g., a segmented block copolymer, a linear alternating multiblock copolymer, a triblock terpolymer, or asymmetric tetrablock terpolymers). The hard and soft segments of the respective block polymers can have the same molecular structure. In certain implementations, the hard segments of the respective block polymers include methylene diisocyantate and butane diol. The soft segment of each respective block polymer can be synthesized from oligomer diols, as an example In certain implementations, the soft segment of each block polymers is a copolymer of a first monomer and a second monomer and the comonomer ratio of the first monomer to the second monomer is varied in combination with the hard segment to soft segment ratio. The first monomer can be dimethyl siloxane and the second monomer can be hexamethylene carbonate. In some implementations, the soft segments of each block polymer are synthesized from oligomer diols. In certain implementations, the soft segments of each block polymer include polydimethylsiloxane. The soft segments of each of the first and second segmented block copolymers can be hydrophilic. For example, the soft segments of each of the block polymers can be hydrophobic (e.g., polydimethylsiloxane). In some implementations, the block polymers are each thermoplastic elastomers.

In some implementations, one or more of the at least two polymers is a polyurethane block polymer and/or a polyurethane urea block polymer.

In certain implementations, one or more of the at least two polymers is one or more of the following: polycarbonate urethane; poly(dimethylsiloxane urethane); and poly(isobutylene urethane).

In some implementations, one of the at least two polymers is a surface coating disposed over at least a portion of another one or more of the at least two polymers, along at least one side of the leaflet extending from the root portion to the edge portion. The surface coating can be a polyurethane with surface active end groups and/or a polyurethane urea with surface active end groups. In some implementations, the surface coating is polyurethane and/or polyurethane urea with polyethylene oxide soft segments. Additionally or alternatively, the surface coating can be a drug-releasing layer. Additionally or alternatively, the surface coating can have a different elastic modulus, compared to the one or more polymers that it covers.

In certain implementations, each of the at least two polymers has respective hard and soft segments, the hard and soft segments of the surface coating having the same molecular structure as the respective hard and soft segments of the other of the at least two polymers, and the surface coating includes surface active end groups. The surface active end groups can include non-polar surface active end groups—e.g., one or more of the following: fluorocarbon, dimethylsiloxane, and hydrocarbon. Additionally or alternatively, the surface active end groups include polar surface active end groups. In some implementations, the surface active end groups include glycosaminoglycan and/or polysaccharides. In certain implementations, the surface active end groups include polyethylene oxide, hyaluronic acid, and heparin.

In some implementations, a skirt is disposed about the base. The skirt can reduce and, in some cases, prevent paravalvular leaks. The base defines a concentric passage therethrough, and the skirt is eccentrically arranged relative to the concentric passage of the base. The skirt can include one or more of the at least two polymers, and can be integral with the base.

In certain implementations, the base defines a passage therethrough and the plurality of leaflets are disposed within the passage. The base can include one or more of the at least two polymers. Additionally or alternatively, the base can include a stent (e.g., a self-expandable stent or a balloon-expandable stent) at least partially embedded in one or more of the at least two polymers. In some implementations, the base is substantially cylindrical, and the base has a height of about 5 mm to about 20 mm.

In some implementations, the plurality of leaflets includes three leaflets movable between an open position permitting flow of fluid past the prosthetic heart valve and a closed position substantially restricting flow past the prosthetic heart valve.

In certain implementations, each of the plurality of leaflets further includes fibers at least partially embedded in one or more of the at least two polymers. The fibers can be oriented to achieve certain mechanical properties (e.g., stiffness). This includes fiber orientations resulting in anisotropic mechanical properties. Each of the fibers can extend substantially parallel or substantially perpendicular to a direction extending from the root portion to the edge portion of the respective leaflet. Additionally or alternatively, a first portion of the fibers can extend substantially parallel to a direction extending from the root portion to the edge portion of the respective leaflet and a second portion of the fibers can extend substantially perpendicular to a direction extending from the root portion to the edge portion of the respective leaflet. In some implementations, the leaflets have one or more anisotropic mechanical properties (e.g., stiffness). In certain implementations, the fibers are substantially randomly embedded in one or more of the first and second polymers.

In some implementations, the fibers include one or more of the following: an ultra-high-molecular-weight polyethylene, liquid crystalline polymer, and NiTi wire.

In another aspect, a prosthetic heart valve includes a base and a plurality of polymeric leaflets. Each leaflet has a root portion coupled to the base, and each leaflet has an edge portion substantially opposite the root portion and movable relative to the root portion to coapt with a respective edge portion of at least one of the other leaflets of the plurality of leaflets. Each leaflet includes a polymer and fibers at least partially embedded in the polymer.

In some implementations, the base defines a substantially cylindrical passage extending therethrough, and the plurality of leaflets is disposed in the cylindrical passage.

In certain implementations, the fibers are substantially parallel to a radial direction or a circumferential direction of the cylindrical passage.

In some implementations, the fibers are arranged in a matrix with at least a portion of the fibers oriented in a direction substantially parallel to a radial direction of the cylindrical passage and at least a portion of the fibers oriented in a direction substantially parallel to a circumferential direction of the cylindrical passage.

In certain implementations, the leaflets have one or more anisotropic mechanical properties (e.g., stiffness).

In some implementations, the fibers are substantially randomly embedded in the polymer.

The fibers can include one or more of the following: a polyester, an ultra-high-molecular-weight polyethylene, liquid crystalline polymer, and NiTi wire.

In yet another aspect, a method of forming a prosthetic heart valve includes forming a base defining a substantially cylindrical passage therethrough, forming a plurality of leaflets, and coupling each of the plurality of leaflets to the base. Each leaflet has a root portion and an edge portion substantially opposite the root portion. Each leaflet includes at least two polymers, and each leaflet has a composition gradient of the at least two polymers along at least one portion of the leaflet. The root portion of each leaflet is coupled to the base such that each respective edge portion is substantially opposite the root portion and movable relative to the root portion to coapt with a respective edge portion of at least one of the other leaflets of the plurality of leaflets.

In certain implementations, forming the base includes applying one or more of the at least two polymers to at least one portion of a stent. For example, forming the base can include one or more of spray coating, dip coating, and vacuum forming one or more of the at least two polymers to at least one portion of a stent and/or to a mold. The at least two polymers can be dried and, in implementations in which a mold is used, the base can be removed from the mold. In some implementations, dip coating one or more of the at least two polymers on a mold includes repeatedly dipping the mold into one or more polymer solutions. Additionally or alternatively, dip coating one or more of the at least two polymers on the mold includes masking at least a portion of the mold.

In certain implementations, forming the plurality of leaflets includes spray coating one or more of the at least two polymers on a mold. Spray coating one or more of the at least two polymers on the mold can include applying the one or more of that at least two polymers as a multi-layer spray coating. Additionally or alternatively, spray coating one or more of the at least two polymers on the mold can include spray coating one or more of the at least two polymers on a mandrel disposed in the substantially cylindrical passage defined by the base.

In some implementations, spray coating the at least two polymers on the mold includes controlling the ratio of one of the at least two-polymers to another one of the at least two-polymers along various locations along the mold. In certain implementations, spray coating the at least two polymers on the mold includes controlling the thickness of one or more of the at least two polymers at various locations along the mold.

In some implementations, spray coating one or more of the at least two polymers on the mold includes delivering one of the at least two polymers from a first spray head and delivering another one of the at least two polymers from a second spray head. Additionally or alternatively, spray coating one or more of the at least two polymers on the mold can include changing the position of the mold relative to the first and second spray heads. In certain implementations, spray coating one or more of the at least two polymers on the mold comprises delivering one or more of the at least two polymers through a three-dimensional printing system, air spraying one or more of the at least two polymers on the mold, and/or electrostatically spraying one or more of the at least two polymers on the mold.

In certain implementations, forming the plurality of leaflets includes dip coating the one or more of the at least two polymers on a mold. Dip coating one or more of the at least two polymers on the mold can include repeatedly dipping the mold in one or more polymer solutions, each polymer solution comprising a solvent and one or more of the at least two polymers. One or more of the at least two polymers can be dried on the mold between successive dips of the mold in the one or more polymer solutions. In some implementations, the thickness and/or stiffness of the leaflet is controlled by controlling a dip rate of the mold into the one or more polymer solutions. Additionally or alternatively, the thickness and/or stiffness of the leaflet can be controlled by controlling an evaporation rate of one or more of the solvents in the respective polymer solutions.

In some implementations, dip coating one or more of the at least two polymers on the mold includes dip coating one or more of the at least two polymers on a mandrel disposed in the substantially cylindrical passage defined by the base.

In certain implementations, dip coating the at least two polymers on the mold includes controlling the ratio of one of the at least two polymers to another one of the at least two polymers along various locations along the mold and/or controlling the thickness of one or more of the at least two polymers at various locations along the mold.

In some implementations, dip coating the at least two polymers on the mold includes masking at least a portion of the mold.

In certain implementations, dip coating the at least two polymers on the mold includes partially submerging the mold in a polymer solution comprising a solvent and one or more of the at least two polymers.

In some implementations, forming the plurality of leaflets comprises vacuum forming one or more of the at least two polymers on a mold. For example, one or more of the at least two polymers can be a film.

In certain implementations, forming the plurality of leaflets further includes cutting at least a portion of one or more of the at least two polymers. Cutting at least a portion of one or more of the at least two polymers can include directing one or more lasers at one or more of the at least two polymers. Additionally or alternatively, cutting at least a portion of one or more of the at least two polymers includes directing a blade at one or more of the at least two polymers.

In some implementations, forming the plurality of leaflets includes arranging a wall in the substantially cylindrical passage and applying the at least two polymers on either side of substantially planar surfaces of the wall. The plurality of leaflets can be formed by removing the wall from the substantially cylindrical passage. In certain implementations, forming the plurality of leaflets includes removing excess amounts of one or more of the at least two polymers on either side of the substantially planar surfaces of the wall. The wall can be a shim and/or the wall can include a thick portion and a thin portion such that the spacing between the plurality of formed leaflets is variable from the base to a center portion of the substantially cylindrical passage.

In certain implementations, coupling the root portion of each of the plurality of leaflets to the base includes applying (e.g., spray coating) one or more of the at least two polymers between the root portion of each of the plurality of leaflets and the base.

In some implementations, a surface coating (e.g., a polyurethane with surface active end groups) is applied over at least a portion of one or more of the at least two polymers. In certain implementations, the at least two polymers and the surface coating each include respective hard and soft segments, the hard and soft segments of the at least two polymers and the surface coating have the same molecular structure, and the surface coating further includes surface active end groups.

In certain implementations, forming the plurality of leaflets includes at least partially embedding a plurality of fibers in one or more of the at least two polymers. For example, forming the plurality of leaflets can include arranging each of the fibers in a direction substantially parallel or substantially perpendicular to a direction extending from the root portion to the edge portion of the respective leaflet. In some implementations, forming the plurality of leaflets further includes arranging a first portion of the fibers in a direction extending substantially parallel to a direction extending from the root portion to the edge portion of the respective leaflet and a second portion of the fibers extending in a direction substantially perpendicular to a direction extending from the root portion to the edge portion of the respective leaflet. In certain implementations, forming the plurality of leaflets further includes arranging the plurality of fibers in each respective leaflet such that each leaflet has one or more anisotropic mechanical properties (e.g., stiffness). In some embodiments, the fibers include one or more of an ultra-high-molecular-weight polyethylene, a liquid crystalline polymer, and a NiTi wire.

Implementations can include one or more of the following advantages.

In some implementations, prosthetic heart valves include a plurality of polymeric leaflets, each including a composition gradient of at least two polymers along a portion of each leaflet. This composition gradient of each of the at least two polymers can improve the durability of the leaflets with respect to leaflets formed of a single polymer. Additionally or alternatively, this composition gradient of the at least two polymers can improve the hemodynamic performance (e.g., by matching natural hemodynamic performance and/or through improved durability) of each leaflet as compared to leaflets formed of a single polymer at least because the composition gradient allows each leaflet to have a desired stiffness profile. In some instances, the composition gradient can reduce the overall thickness of each leaflet as compared to leaflets formed of a single polymer or biological tissue such that a prosthetic heart valve including polymeric leaflets having this composition gradient have smaller delivery profiles for transcatheter delivery.

In certain implementations, prosthetic heart valves include a plurality of polymeric leaflets coupled to a base without the use of sutures. As compared to valves that require the use of sutures to secure leaflets, these sutureless prosthetic heart valves can be less labor intensive to produce and can have less manufacturing variability. Additionally or alternatively, as compared to valves that require the use of sutures to secure leaflets, these sutureless prosthetic heart valves can exhibit improved durability.

In some implementations, prosthetic heart valves include a plurality of leaflets, each leaflet including fibers at least partially embedded in a polymer. The fibers can be arranged along each leaflet to provide support and/or desired mechanical properties (e.g., anisotropic mechanical properties) to each leaflet. In some instances, these fibers can facilitate the use of a thinner layer of the polymer as compared to polymeric leaflets formed without these fibers. Such thinner layers can facilitate that formation of prosthetic heart valves having smaller delivery profiles for transcatheter delivery.

In certain implementations, the prosthetic heart valves include a plurality of polymeric leaflets formed of at least two polymers, one of the at least two polymers having hard and soft segments having the same molecular structure as hard and soft segments of another one of the at least two polymers, with the ratio of hard segments to soft segments in one of the at least two polymers being higher than the ratio of hard segments to soft segments in another one of the at least two polymers. The use of two polymers having the same molecular structure can reduce the likelihood of delamination or other mechanical failure of the polymeric leaflets while facilitating formation of the leaflets with variable stiffness from a root portion to an edge portion.

In certain implementations, the prosthetic heart valves include a plurality of polymeric leaflets formed of at least two polymers, one of the at least two polymers having hard and soft segments having a certain molecular structure and another one of the at least two polymers having either the same hard segment but different soft segment or different hard segment but same soft segment. (e.g. polyisobutylene polyurethane (PIBU) and/or poly(styrene-block-isobutylene-block-styrene (SIBS)). Since these polymers have a common hard segment or soft segment, coating one layer over a second layer will have eliminated the possibility of delamination because of the molecular miscibility as a result of the common structure. The use of two polymers having a common hard segment or soft segment structure can reduce the likelihood of delamination or other mechanical failure of the polymeric leaflets while facilitating formation of the leaflets with variable stiffness from a root portion to an edge portion. Additionally or alternatively, the use of two polymers having a common hard segment or soft segment structure can facilitate control of the mechanical properties and surface properties of the device.

In some implementations, the prosthetic heart valves are easier to manufacture, are more reproducible, and have a lower height as compared to mechanical heart valves and/or heart valves at least partially formed from biological tissue.

The details of one or more implementations of the invention are set forth in the accompanying drawings and the description below. Other features, objects, and advantages of the invention will be apparent from the description and drawings, and from the claims.

DESCRIPTION OF DRAWINGS

FIG. 4A is a schematic illustration of repeated hard segments and soft segments of a polymer forming a leaflet of a prosthetic heart valve.

FIG. 4B is a schematic illustration of the polymer of FIG. 4A having a first ratio of hard segments to soft segments.
FIG. 4C is a schematic illustration of the polymer of FIG. 4A having a second radio of hard segments to soft segments.

Like reference symbols in the various drawings indicate like elements.

DETAILED DESCRIPTION

Figure 1:
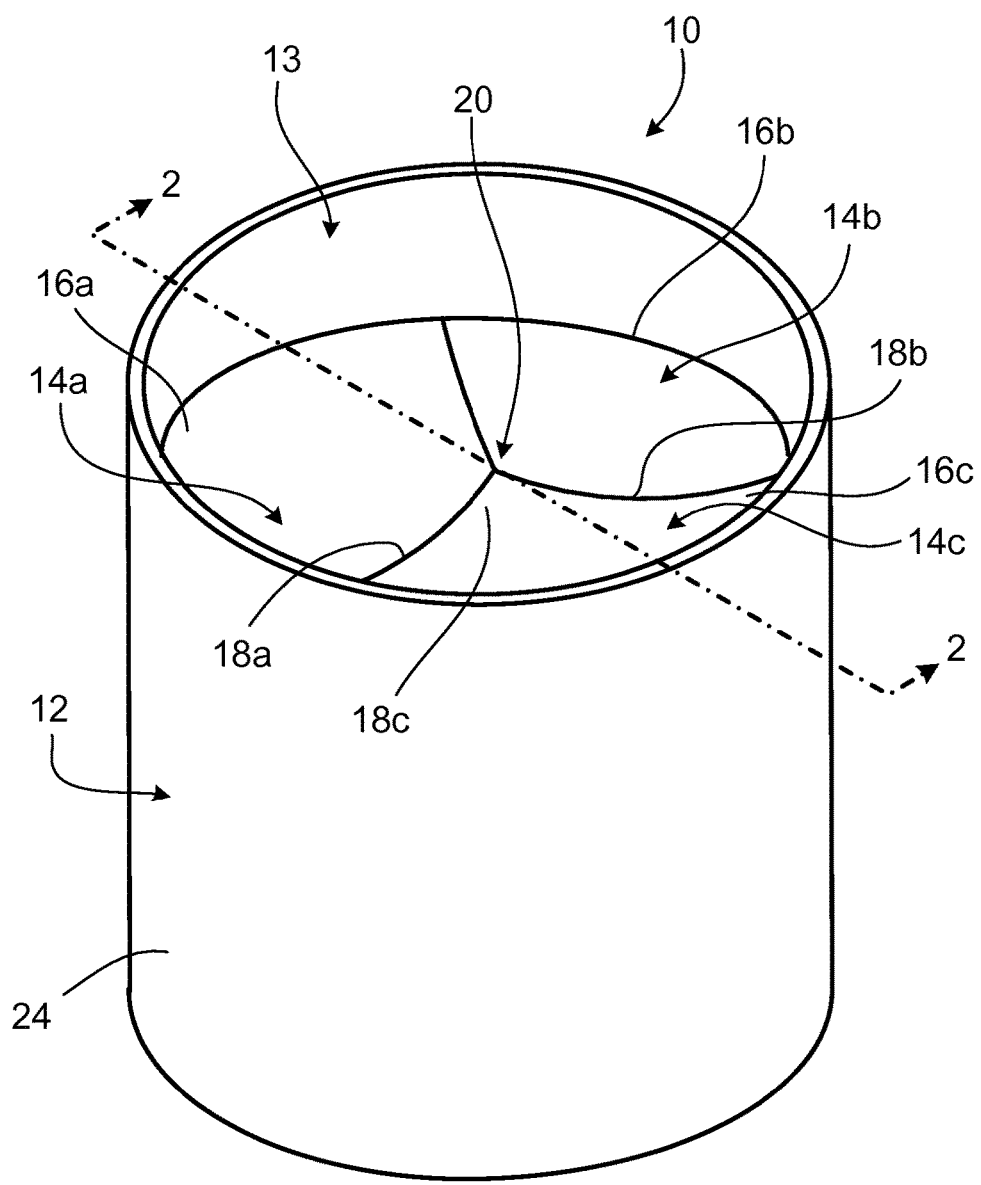
FIG. 1 is a perspective view of a prosthetic heart valve.
Figure 2:
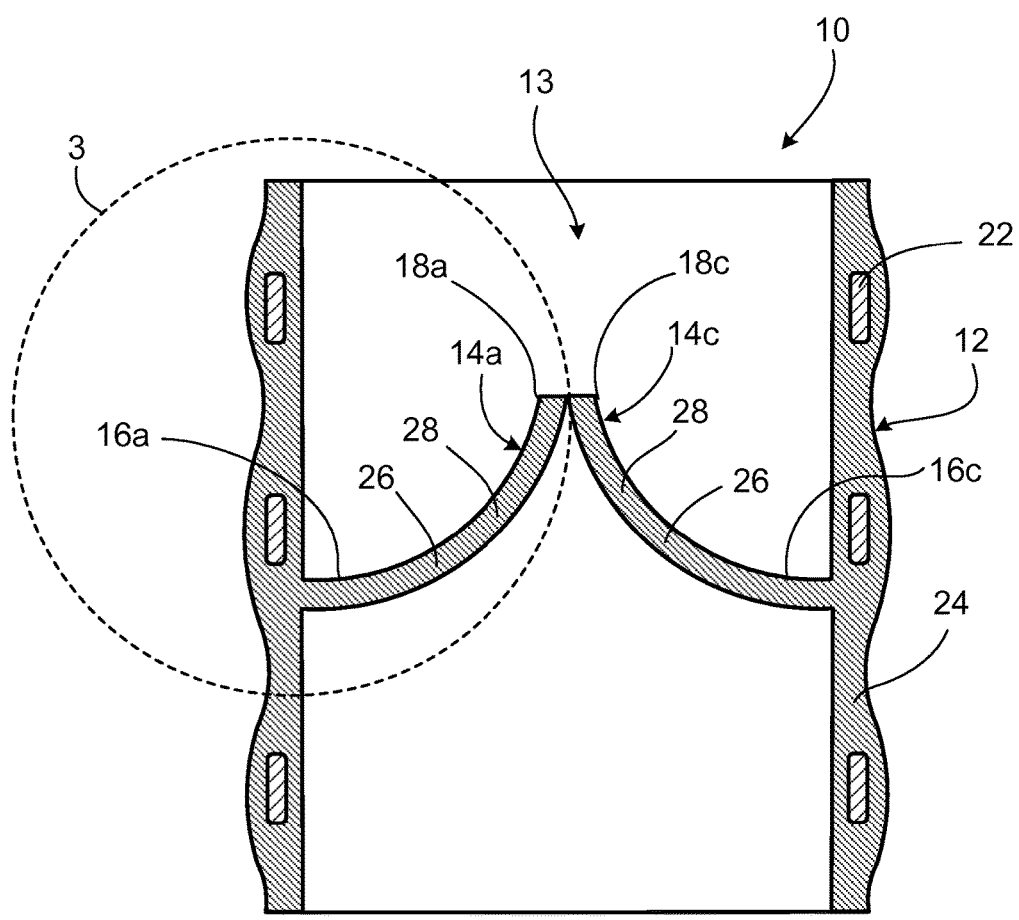
FIG. 2 is a cross-sectional view of the prosthetic heart valve of FIG. 1, along line 2-2.
Figure 3:
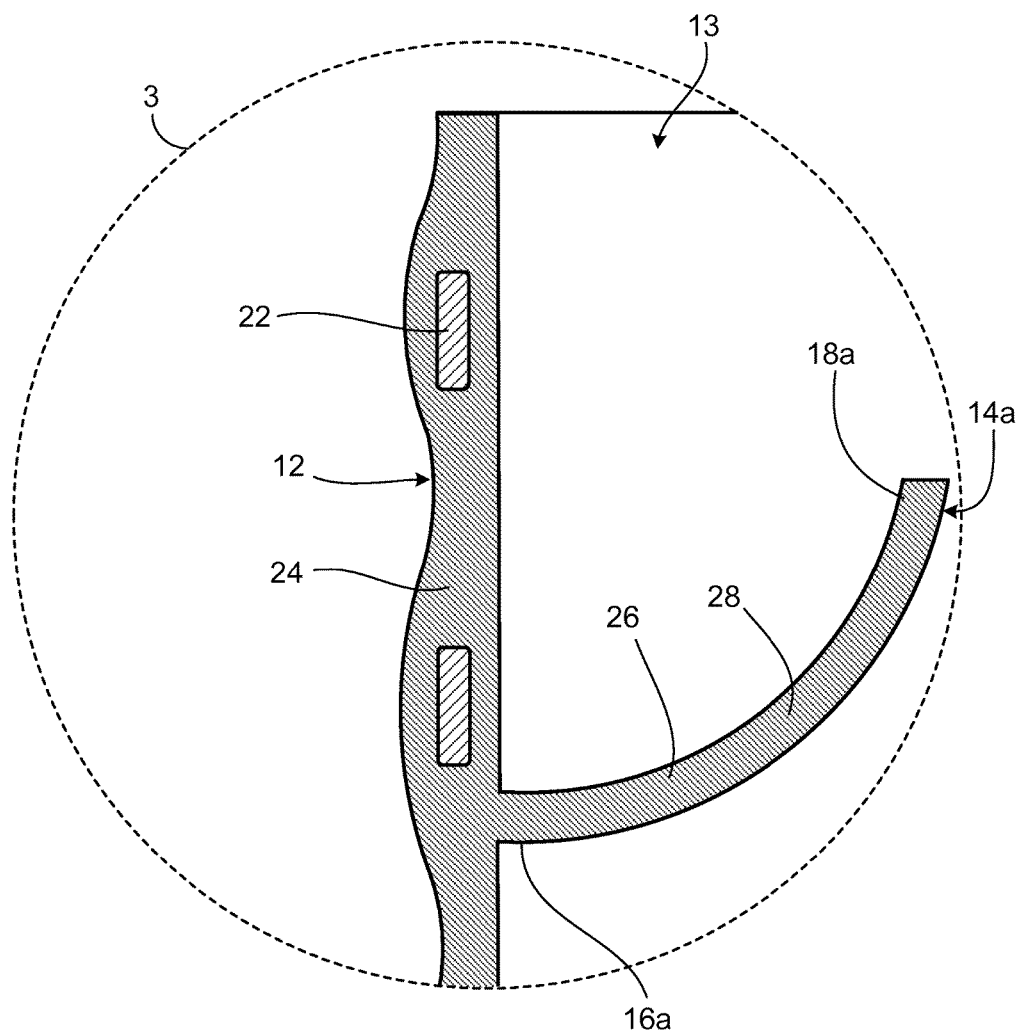
FIG. 3 is a close-up of a cross-section of a polymeric leaflet of the prosthetic heart valve of FIG. 2 along circle 3.

Referring to FIGS. 1-3 a prosthetic heart valve 10 includes a base 12 defining a substantially cylindrical passage 13 and a plurality of polymeric leaflets 14 $a,b,c$ disposed along the substantially cylindrical passage 13. Each polymeric leaflet 14$a,b,c$ includes a respective root portion 16$a,b,c$ coupled to the base 12 and a respective edge portion 18$a,b,c$ movable relative to the root portion 16$a,b,c$ to coapt with the edge portions of the other polymeric leaflets along the coaptation region 20. It should be appreciated that the prosthetic heart valve 10 can be any type of heart valve (e.g., a mitral valve or an aortic valve).

In use, the prosthetic heart valve 10 is implanted (e.g., surgically or through transcatheter delivery) in a mammalian heart. The edge portions 18$a,b,c$ of the polymeric leaflets 14$a,b,c$ move into coaptation with one another in a closed position to substantially restrict fluid from flowing past the prosthetic heart valve 10 in a closed position. The edge portions 18$a,b,c$, of the leaflets 14$a,b,c$ move away from one another to an open position permitting fluid to flow past the prosthetic heart valve 10. Movement of the leaflets 14$a,b,c$ between the closed and open positions substantially approximates the hemodynamic performance of a healthy natural valve.

As described in further detail below, the polymeric leaflets 14$a,b,c$ are formed from a combination of at least two polymers, which can be arranged along each respective polymeric leaflets 14$a,b,c$ to facilitate achievement of a desired hemodynamic performance of the valve 10 through long periods of use. As also described in further detail below, the polymeric leaflets 14$a,b,c$ can be attached to the base 12 without the use of sutures, which can reduce the time and labor resources required to make the valve and can reduce valve-to-valve variability in hemodynamic performance.

The base 12 includes a frame 22 disposed in a polymer layer 24. The polymer layer 24 secures the respective root portions 16a,b,c of the polymeric leaflets 14a,b,c to the base 12. The polymer layer 24 can form a substantially continuous surface with the respective root portions 16a,b,c of the polymeric leaflets 14a,b,c. This can reduce the likelihood of stress concentrations at the junction of the respective root portions 16a,b,c and the base 12. Additionally or alternatively, the polymer layer 24 can be disposed between each of the polymeric leaflets 14a,b,c and the frame 22 such that the polymer layer 24 protects the polymeric leaflets 14a,b,c from inadvertent contact with the frame 22 (e.g., as can occur through eccentric deformation of the prosthetic heart valve 10 on a calcium deposit present at the implantation site).

The frame 22 is substantially cylindrical such that the outer surface of the base 12 is substantially cylindrical and the polymer layer 24 disposed on the frame 22 forms the substantially cylindrical passage 13. The frame can be metal and, additionally or alternatively, the frame 22 can provide a radial force sufficient to at least partially secure the valve 10 in place at the implantation site. In some implementations, the frame 22 is radially expandable from a collapsed position (e.g., for transcatheter delivery) to an expanded position (e.g., for positioning at the implantation site). For example, the frame 22 can be a self-expandable stent or a balloon-expandable stent.

The frame 22 is completely disposed in the polymer layer 24, with the polymer layer 24 forming a contoured outer surface of the valve 10. However, in some implementations, the frame 22 is partially disposed in the polymer layer 24. In certain implementations, the polymer layer 24 is applied to the frame 22 to form a substantially smooth inner and/or outer surface of the valve 10.

The polymer layer 24 and the leaflets 14a,b,c, are formed of one or more polymers having the same or substantially the same chemical composition, which can reduce the likelihood of delamination and/or other types of degradation at the juncture of the polymer layer 24 and the root portions 16a,b,c of the polymeric leaflets 14a,b,c. For example, the polymer layer 24 and/or the polymeric leaflets 14a,b,c can be formed of a first polymer and a second polymer, the first polymer having hard and soft segments having a certain molecular structure and the second polymer having either the same hard segment but different soft segment or different hard segment but same soft segment (e.g. polyisobutylene polyurethane (PIBU) and/or poly(styrene-block-isobutylene-block-styrene) (SIBS)). Since these polymers have a common hard segment or soft segment, coating one layer over a second layer will reduce (e.g., eliminate) the possibility of delamination because of the molecular miscibility as a result of the common structure. The use of two polymers having a common hard segment or soft segment structure can reduce the likelihood of delamination or other mechanical failure of the polymeric leaflets 14a,b,c while facilitating formation of the leaflets with variable stiffness from a root portion to an edge portion. Additionally or alternatively, the use of two polymers having a common hard segment or soft segment structure can facilitate control of the mechanical properties and surface properties of the device. The polymers in the polymer layer 24 and the leaflets 14a,b,c are described in further detail below.

Given that the root portions 16a,b,c are secured to the polymer layer 24 and, thus, the base 12 without the use of sutures, the base 12 can be formed without support portions typically required on sutured valves. This can facilitate formation of the prosthetic heart valve 10 with a lower overall height as compared to sutured valves. Such lower overall height can improve the hemodynamic performance of the prosthetic heart valve as compared to valves having larger overall heights. Additionally or alternatively, the lower overall height facilitated by the formation of the prosthetic heart valve 10 without sutures can improve the physiological performance of the prosthetic heart valve 10 as compared to valves having larger overall heights. For example, the base 12 can define an overall height of the prosthetic heart valve 10 and the height of the base 12 can sized such that the coronary ostium is not covered by the prosthetic heart valve 10 at the implantation site. This can, for example, reduce the likelihood of disrupting normal electrical signaling in the heart. In some implementations, the base 12 has an overall height of about 5 mm to about 20 mm, depending on the diameter of the cylindrical valve body.

The polymeric leaflets 14a,b,c each have a substantially uniform thickness and a composition gradient of a first polymer 26 and a second polymer 28 along a length of the leaflet extending from each respective root portion 16a,b,c to the respective edge portion 18a,b,c. As described in detail below, the first polymer 26 and the second polymer 28 can be block polymers each having the same molecular structure but different ratios of hard segments to soft segments such that the first polymer 26 is stiffer than the second polymer 28. Thus, the composition gradient of the first polymer 26 and the second polymer 28 can be an increase (e.g., a substantially continuous increase) in the ratio of the second polymer 28 to the first polymer 26 in a direction extending generally from the root portion 16a,b,c to the edge portion 18a,b,c of each respective leaflet 14a,b,c such that each leaflet is stiffer toward the root portion 16a,b,c and more flexible toward the edge portion 18a,b,c. It should be appreciated that the polymeric leaflets 14a,b,c are described as including the first polymer 26 and the second polymer 28 for the sake of clarity of description. A third polymer, a fourth polymer, fifth polymer, etc. could be used.

The natural anatomical construction of a heart valve is such that there are anisotropic mechanical properties. The structure of the native leaflet is a trilayer construct. On the side facing the ventricle, there is a layer of collagen and elastin fibers with a radial orientation (aligned from the wall of the supporting structure to the tip of the valve leaflet). In the fibrosa layer (the side facing the aorta) there is collagen but the fibers are oriented more circumferentially, which imparts characteristic flexibility and enables valve sealing. It should be appreciated that the composition gradient of the first and second polymers 26, 28 can be varied along the leaflets 14a,b,c to substantially match the anisotropic mechanical properties of healthy, native leaflets.

Compared to leaflets formed of a single polymer, the composition gradient of the first and second polymers 26, 28 can facilitate formation of thin polymeric leaflets 14a,b,c that also exhibit stiffness characteristics similar to stiffness characteristics of healthy, natural leaflets. For example, the polymeric leaflets 14a,b,c can have a substantially uniform thickness of less than about 100 μm and exhibit anisotropic mechanical properties similar to those of healthy, natural leaflets.

Additionally or alternatively, polymeric leaflets 14a,b,c can have improved durability as compared to polymer leaflets formed of a single polymer. For example, the flexibility of the edge portion 18a,b,c of each leaflet 14a,b,c can facilitate valve sealing (e.g., at implantation sites having an irregular cross-sectional area as a result of calcium deposits). As another example, the stiffness of the root portion 16a,b,c of each leaflet 14a,b,c can reduce stress associated with movement of the leaflets 14a,b,c into and out of coaptation with one another.

In some implementations, the composition gradient of the first and second polymers 26, 28 can be an increase in the ratio of the second polymer 28 to the first polymer 26 in a direction extending along a thickness of each leaflet 14a,b,c. In certain implementations, the composition gradient of the first and second polymers 26, 28 can be a pattern (e.g., a sinusoidal pattern) in a direction extending generally from the root portion 16a,b,c to the edge portion 18a,b,c.

In some implementations, the side facing the ventricle, in the implanted position, can include only one of first and second polymers 26, 28 and the side facing the aorta, in the implanted position, can include the other of the first and second polymers 26, 28.

The first polymer 26 is a first block polymer and the second polymer 28 is a second block polymer. Each of the first and second polymers 26, 28 can be a segmented block copolymer, a linear alternating multiblock copolymer, a triblock terpolymer, or an asymetric tetrablock terpolymer. Examples of block polymers are described in Frank S. Bates et al., *Multiblock Polymers: Panacea or Pandora's Box?*, SCIENCE, 336, 434 (2012), the entire contents of which are incorporated herein by reference. Additionally, or alternatively, each of the block polymers is a thermoplastic elastomer. In general, the first polymer 26 and the second polymer 28 each have the same molecular structure and each have hard segments and soft segments. The second polymer 28 has a lower ratio of hard segments to soft segments compared to the first polymer 26. Accordingly, the first polymer 26 is stiffer than the second polymer 28. See B. Zhang et al., EUR. POLYM. J. Vol. 34, No. 3-4, pp. 571-575 (1998), the entire contents of which are incorporated herein by reference.

In some implementations, at least one of the first and second polymers 26, 28 is a polyurethane block polymer (e.g., copolymer) and/or a polyurethane urea block polymer, each of which can be tailored to have desired stiffness and mechanical properties and have good blood compatibility. Examples of suitable polyurethane block polymers include biostable polyurethanes such as polycarbonate urethanes (e.g., Carbothane® available from The Lubrizol Corporation of Wickliffe, Ohio), poly(dimethysiloxane urethanes) (e.g., Elast-Eon polymers from AorTech International plc of Weybridge, Surrey, England), and/or poly(isobutylene urethane). Examples of suitable poly(isobutylene urethane) are described in U.S. patent application Ser. No. 12/492,483, filed Jun. 26, 2009, and U.S. patent application Ser. No. 12/685,858, filed Jan. 12, 2010. The entire contents of each of these applications are incorporated herein by reference. In certain implementations, the first and second polymers 26, 28 each include a soft segment that is a copolymer of a first monomer (e.g., dimethyl siloxane) and a second monomer (e.g., hexamethylene carbonate) and the comonomer ratio of the first monomer to the second monomer is varied in combination with the hard segment to soft segment ratio. In some implementations, the soft segment of each of the first and second polymers 26, 28 is hydrophilic. In certain implementations, there is an outer polymer including the same molecular structures for hard segments or soft segments and also including an additional surface active component which can improve endothelialization or reduce calcification or both.

Referring to FIGS. 4A-C, in some implementations, the first polymer 26 and the second polymer 28 each have hard segments 30 that are repeated units of methylene diisocyantate (MDI) and butane diol (BD) and soft segments 32 that are polytetramethylene oxide (PTMO). Comparing the structures in FIGS. 4B and 4C, it can be appreciated that the second polymer 28 has a lower ratio of hard segments to soft segments compared to the first polymer 26 and, thus, the first polymer 26 is stiffer than the second polymer 28.

Referring to FIGS. 5A-D, prosthetic heart valves (e.g., prosthetic heart valve 10) are formed through one or more processes generally including forming a base (e.g., the base 12), forming a plurality of polymeric leaflets (e.g., the polymeric leaflets 14a,b,c shown in FIGS. 1-3), and coupling the plurality of polymeric leaflets to the base such that each leaflet is movable to coapt with a portion of at least one of the other leaflets. For example, a spray-coating process as shown in FIGS. 5A-D can be used to form prosthetic heart valves including a plurality of polymeric leaflets, each having a composition gradient of a first and a second polymer along at least one portion of the leaflet.

Figure 5A:
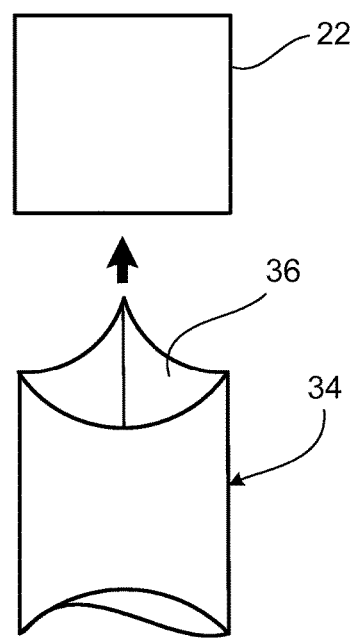
FIGS. 5A-5D are schematic illustrations of steps of spray forming in the formation of a prosthetic heart valve.

Referring to FIG. 5A, a mold 34 (e.g., a mandrel) is positioned in a volume defined by the frame 22 (e.g., a radially expandable stent in an expanded position) such that a leaflet form 36 of the mold 34 is at the position at which the polymeric leaflets 14a,b,c (shown in FIGS. 1-3) are to be formed. In some implementations, the mold 34 is moved into the frame 22. Additionally or alternatively, at least a portion of the frame 22 is formed about the mold 34. The leaflet form 36 includes one or more curved surfaces (e.g., concave surfaces) having the desired shape of each respective leaflet. As described in further detail below, the first polymer 26 and the second polymer 28 (shown in FIGS. 1-3) are sprayed onto the one or more curved surfaces of the leaflet form 36 to form the leaflets 14a,b,c (shown in FIGS. 1-3).

Figure 5B:
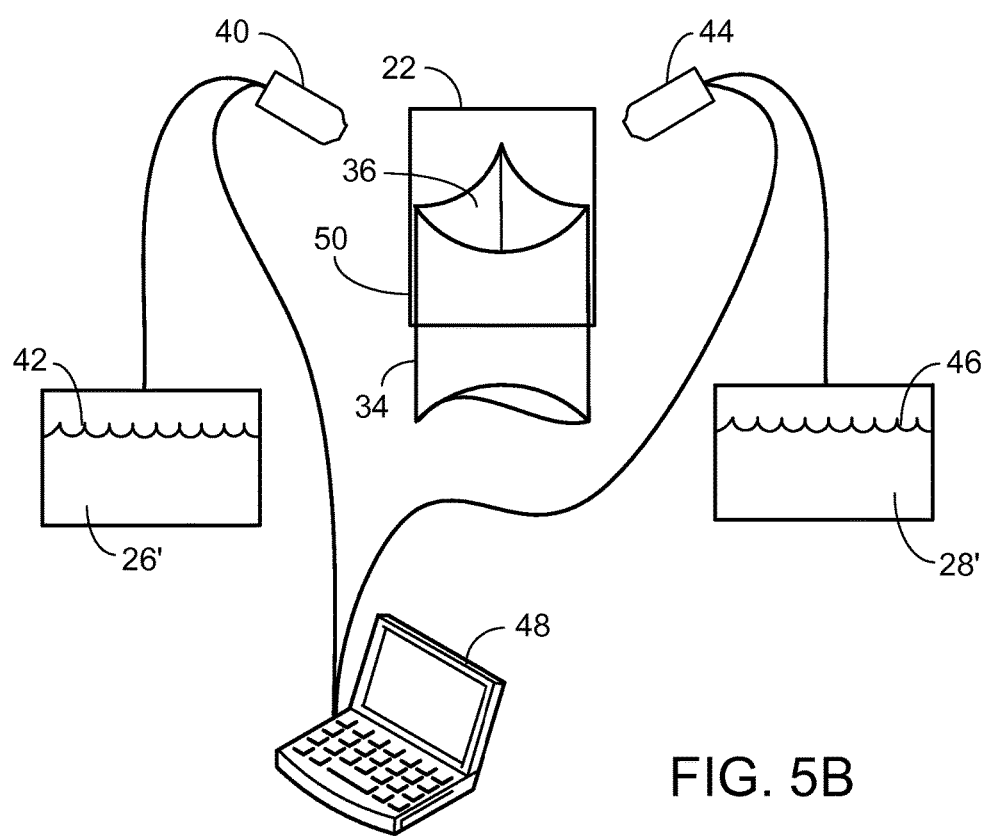

Referring to FIG. 5B, a spray system 38 includes a first spray head 40, a first reservoir 42, a second spray head 44, a second reservoir 46, and a controller 48. The first spray head 40 is in fluid communication with the first reservoir 42 to draw a first solution 26' including the first polymer 26 (FIGS. 1-3) and a solvent from the first reservoir 42 to the first spray head 40 for application to the frame 22 and/or the mold 34. Similarly, the second spray head 44 is in fluid communication with the second reservoir 46 to draw a second solution 28' including the second polymer 28 (FIGS. 1-3) and a solvent from the second reservoir 46 to the second spray head 44 for application to the base and/or the mold 34. The controller 48 is in electrical communication with the first and second spray heads 40, 44 to control, as described in further detail below, the position of the first spray head 40 and the second spray head 44 relative to the frame 22 and/or to control the volume and spray pattern of the respective fluid delivered from the first and second spray heads 40, 44.

The first reservoir 42 and the second reservoir 46 can each be pressurized such that the respective contents of the first and second reservoir 42, 46 can be delivered by controlling a respective nozzle position (e.g., open/closed) of the first and second spray heads 40, 44. The respective solvents (e.g., organic solvents) of the first and second solutions 26', 28' can facilitate achievement of a desired spray pattern of the respective first and second polymers 26, 28 (FIGS. 1-3). For example, a lower concentration of solvent can be used in areas where it is desirable to have less flow, and a higher concentration of solvent can be used in areas where it is desirable to have flow. Additionally alternatively, the respective solvents can have a desired viscosity and/or evaporation rate to achieve desired spreading of the respective polymer on the frame 22 and/or mold 34.

In some implementations, the first spray head 40 and/or the second spray head 44 includes one or more air spray nozzles such that the first solution 26' and/or the second solution 28' are air sprayed on the frame 22 and/or the mold 34. In certain implementations, the first spray head 40 and/or the second spray head 44 includes one or more electrostatic spray nozzles such that the first polymer 26 and/or the second polymer 28 are electrostatically sprayed on the frame 22 and/or the mold 34. In some implementations, such electrostatic spraying can result in the efficient transfer of the first and second polymers 26, 28 (FIGS. 1-3) on the frame 22 and/or mold 34.

The controller 48 includes a central processing unit and a memory and is in electrical communication with the first spray head 40 and the second spray head 44 to control the volumetric emission and spatial distribution of the first polymer 26 and the second polymer 28. The controller 48 can be in electrical communication with the first and second spray heads 40, 44 to control movement of the first and second spray heads 40, 44 relative to the frame 22 and mold 34. Additionally or alternatively, the controller 48 can be in electrical communication with one or more actuators to control movement of the frame 22 and mold 34 relative to the first and second spray heads 40, 44.

Examples of the spray system 38 are described in U.S. Pat. No. 7,335,264, entitled "Differentially Coated Medical Devices, System for Differentially Coating Medical Devices, and Coating Method," issued on Feb. 26, 2008, the entire contents of which are incorporated herein by reference. In some implementations, the spray system 38 is a three-dimensional printing system. For example, the three-dimensional printing system can produce bead-producing drops of the first and/or second polymer 26, 28 at controlled locations (e.g., as determined by one or more position sensors) to build up one or more surfaces (e.g., leaflets 14*a,b,c*).

An inner diameter of the frame 22 is greater than an outer diameter of the mold 34, resulting in a clearance 50 between the frame 22 and the mold 34. The base 12 (FIGS. 1-3) is formed by spraying first and second solutions 26', 28' solutions from the respective first and second spray heads 40, 44 such that the first and the second polymers 26, 28 (FIGS. 1-3) coat the frame 22 and/or the leaflet form 36 of the mold 34. The coating of the first and/or second solutions 26', 28' on the frame 22 forms the polymer layer 24 (FIGS. 1-3). Similarly, the coating of the first and second polymers 26, 28 on the leaflet form 36 forms the shape of the leaflets 14*a,b,c* (FIGS. 1-3).

The composition gradient of the first and second polymers 26, 28 along the leaflets 14*a,b,c* can (FIGS. 1-3) be achieved by controlling the ratio of the volume of the first solution 26' sprayed from the first spray head 40 to the volume of the second solution 28' sprayed from the second spray head 44 along various locations along the leaflet form 36 of the mold 34. Additionally or alternatively, the composition gradient of the first and second polymers 26, 28 (FIGS. 1-3) along the leaflets 14*a,b,c* can be achieved by controlling the thickness of the first and/or the second solutions 26', 28' at various locations along the leaflet form 36 of the mold 34.

Figure 5C:
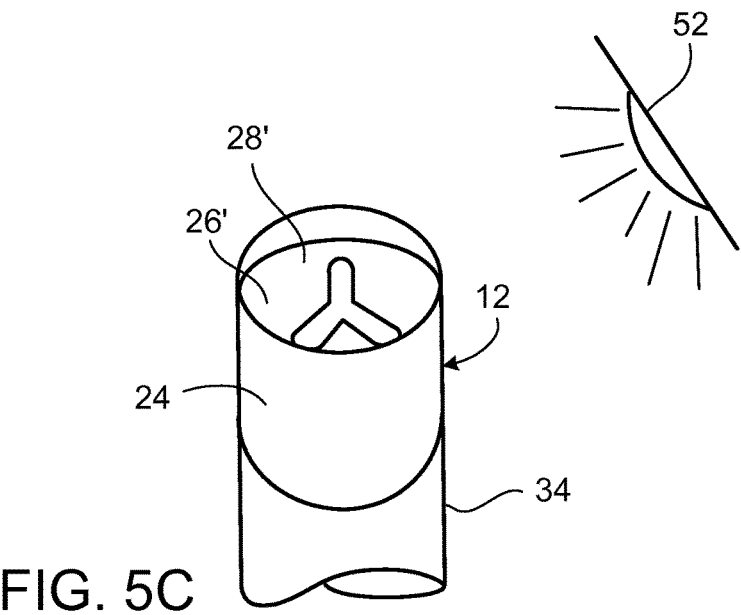

Referring to FIG. 5C, the first and/or second solutions 26', 28' disposed over the frame 22 (FIGS. 1-3) and/or the leaflet form 36 are dried in the presence of a heat source 52. The heat source 52 can be, for example, a convective heat source such as a lamp and/or an oven. The first and second solutions 26', 28' can be exposed to the heat source 52 until evaporation of the solvents used for delivery of the first and second polymers 26, 28 (FIGS. 1-3) is substantially complete.

In some implementations, the first and second polymers 26, 28 are applied to the frame 22 and/or the leaflet form 36 of the mold 34 in multiple layers. For example, the first and second polymers 26, 28 can be applied to the frame and/or the leaflet form 36 in a first layer, the first and second polymers 26, 28 can be dried, and then the first and/or second polymers 26, 28 can be applied in a second layer. The process of applying the first and second polymers 26, 28 to the frame and/or the leaflet form 36 can be repeated to achieve, for example, a desired thickness of the leaflets 14*a,b,c* (FIGS. 1-3).

Figure 5D:
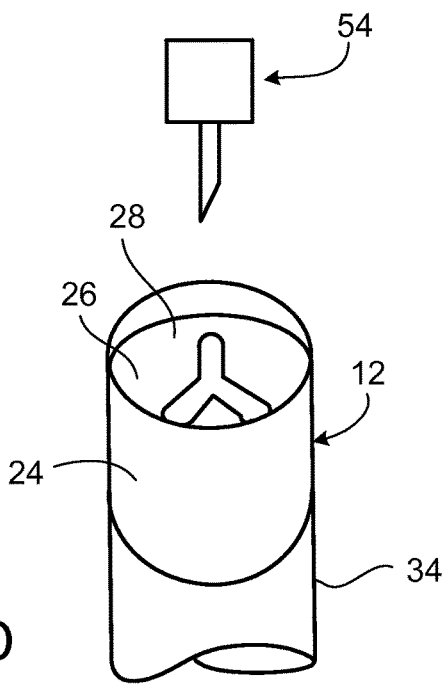

Referring to FIG. 5D, a cutting element 54 is applied to the first and second polymers 26, 28 to form the leaflets 14*a,b,c* from the first and second polymers 26, 28 disposed along the leaflet form 36 of the mold 34. In particular, the cutting element 54 is applied to the first and second polymers 26, 28 to define the edge portions 18*a,b,c* of the respective leaflets 14*a,b,c*. The cutting element 54 can be in electrical communication with the controller 48, with the controller 48 controlling the position of the cutting element 54 relative to the first and second polymers 26, 28.

The cutting element 54 can be a blade movable into contact with the first and second polymers 26, 28 disposed along the leaflet form 36 of the mold 34. For example, the cutting element 54 can be a single blade controlled by the controller 48 to cut the leaflets 14*a,b,c* from the first and second polymers 26, 28 through a sequence of movements. As another example, the cutting element 54 can be three blades controlled by the controller 48 to cut the polymeric leaflets 14*a,b,c* from the first and second polymers 26, 28 with a single motion of the cutting element 54.

Additionally or alternatively, the cutting element 54 can be a laser (e.g., a $CO_2$ laser, a femtosecond laser, or an excimer laser) directed at the first and second polymers 26, 28 disposed along the leaflet form 36 of the mold. As compared to cutting with a blade, cutting the first and second polymers 26, 28 with a laser can reduce the likelihood of fraying, delamination, or other physical changes that may interfere with coaptation of the polymeric leaflets 14*a,b,c* along the edge portions 18*a,b,c*.

In some implementations, the mold 34 is be removed from the base 12 following the drying process (FIG. 5C) and prior to cutting the leaflets 14*a,b,c*. In other implementations, the mold 34 remains adjacent to the base 12 to provide support to the first and second polymers 26,28 as the cutting element 54 is applied to the first and second polymers 26,28 to form the edge portion 18*a,b,c* of each leaflet 14*a,b,c*.

While certain implementations have been described, other implementations are possible.

Figure 6:
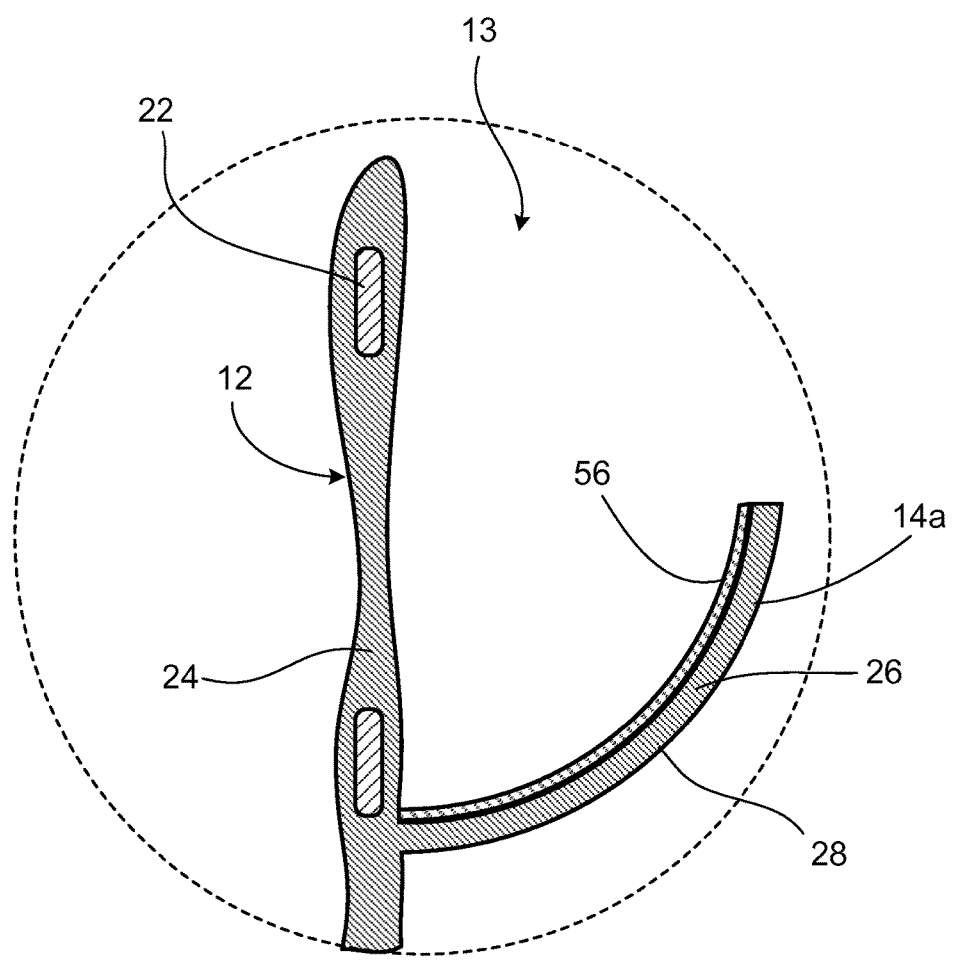
FIG. 6 is a close-up of a cross-section of a polymeric leaflet of a prosthetic heart valve.

For example, while the polymeric leaflets have been described as being uncoated, other implementations are additionally or alternatively possible. For example, referring to FIG. 6, for example, a surface coating 56 can be disposed along at least one side of each leaflet 14*a,b,c* extending from each respective root portion 16*a,b,c* to each respective edge portion 18*a,b,c*. It should be appreciated that, for the sake of clarity of illustration, leaflet 14*a* is shown in FIG. 6 and leaflets 14*b,c* (FIGS. 1-3) can be substantially identical to leaflet 14*a*.

The surface coating 56 can be disposed over the first polymer 26 and/or the second polymer 28. The surface coating 56 can improve the calcification resistance of the leaflets 14*a,b,c*. In some implementations, the surface coating 56 can facilitate maintenance of desirable mechanical properties and stability of the first and second polymers 26, 28 forming the leaflets 14a,b,c. In certain implementations, the surface coating can provide enhanced biocompatibility.

In some implementations, the surface coating 56 includes hard and soft segments having the same molecular structure as the respective hard and soft segments of the first polymer 26 and/or the second polymer 28, with the surface coating 56 further including a small percentage of surface active end groups. Having the same hard and soft segments can ensure intimate bonding with the first and/or second polymers 26, 28 of the leaflets 14a,b,c. Examples of polymers that can be used in the surface coating 56 include polyurethane with surface active end groups and/or polyurethane urea with surface active end groups. Examples include Self Assembling Monolayer Endgroups (SAME®) available from DSM Biomedical, Berkeley, Calif., Surface Modifying Endgroups (SME®) available from DSM Biomedical, Berkeley, Calif., and Tecophilic® polyurethane available from The Lubrizol Corporation of Wickliffe, Ohio. The surface active end groups of the surface coating 56 can include non-polar surface active end groups—e.g., one or more of fluorocarbon, dimethylsiloxane, and hydrocarbon. Additionally or alternatively, these surface active end groups can include glycosaminoglycan and/or polysaccharide. In certain implementations, these surface active end groups include polar surface active end groups—e.g., one or more of polyethylene oxide, hyaluronic acid, and heparin. Additional or alternative examples of polymers that can be used in the surface coating 56 include polyurethane and/or polyurethane urea with polyethylene oxide soft segments.

In certain implementations, the surface coating 56 is a drug-releasing layer.

Figure 7:
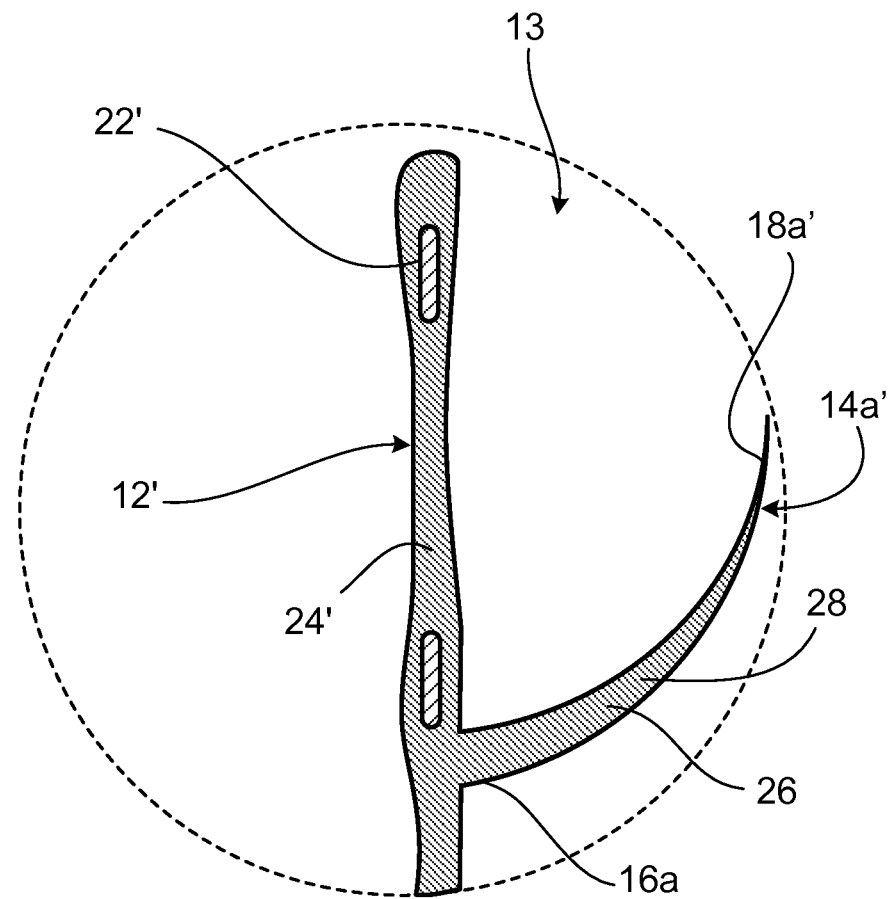
FIG. 7 is a close-up of a cross-section of a polymeric leaflet of a prosthetic heart valve.

As another example, while the polymeric leaflets have been described as having a substantially uniform thickness, other implementations are additionally or alternatively possible. For example, with reference to FIG. 7, leaflet 14a' has a decreasing thickness in a direction extending generally from a root portion 16a' to an edge portion 18a'. For the sake of clarity of illustration, a single leaflet is shown in FIG. 7. However, it should be appreciated that the other leaflets may have the same geometry. It should further be appreciated that, unless otherwise specified, components identified by prime reference numbers (e.g., 14a') are similar to the corresponding component identified by an unprimed reference number (e.g., 14a) in FIGS. 1-3.

The thicker root portion 16a' can impart stiffness to the leaflet 14a' at the point of attachment to the base 12', and the thinner edge portion 18a' can have increased flexibility relative to the root portion 16a'. Such a thickness gradient, alone or in combination with a composition gradient of the first polymer 26 and the second polymer 28, can improve durability and/or hemodynamic performance of the leaflet 14a' relative to a leaflet formed of a single polymer of uniform thickness. In some implementations, the root portion 16a' is about 1000 percent thicker than the edge portion 18a'.

Figure 8:
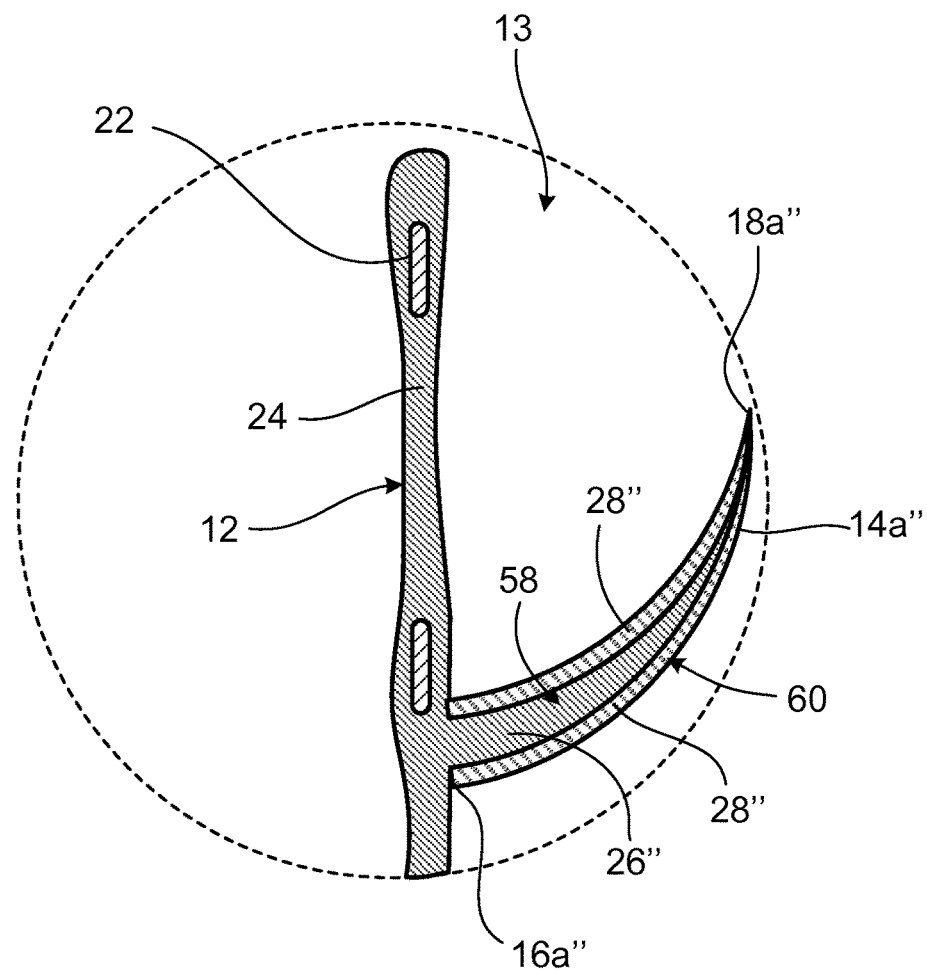
FIG. 8 is a close-up of a cross-section of a polymeric leaflet of a prosthetic heart valve.

As another example, while the composition gradient of the polymeric leaflets have been described as being a mixture of a first polymer and a second polymer, other implementations are additionally or alternatively possible. For example, referring to FIG. 8, a polymeric leaflet 14a" includes a first layer 58 of a first polymer 26" and one or more second layers 60 of a second polymer 28". In some implementations, the first layer 58 is disposed between the one or more second layers 60. For the sake of clarity of illustration, a single leaflet is shown in FIG. 8. However, it should be appreciated that the other leaflets may have the same geometry. It should further be appreciated that, unless otherwise specified, components identified by a double prime reference number (e.g., 14a") are similar to the corresponding component identified by an unprimed reference number (e.g., 14a) in FIGS. 1-3.

In some implementations, each of the first and second layers 58, 60 extends in a direction generally from a root portion 16a" to an edge portion 18a" of the leaflet 14a". For example, each layer 58, 60 can extend along an entire length of the leaflet 14a" from the root portion 16a" to the edge portion 18a". The stiffness of the leaflet 14a" can be varied by varying the ratio of the thickness of the first layer 58 to the thickness of the second layer 60. For example, the thickness of the first layer 58 can taper downward from the root portion 16a" to the edge portion 18a", and the thickness of the second layer 60 can taper upward from the root portion 16a" to the edge portion 18a". In such examples, given that the first polymer 26" is stiffer than the second polymer 28", the polymeric leaflet 14a" can be stiffer toward the root portion 16a" and more flexible toward the edge portion 18a".

Figure 9:
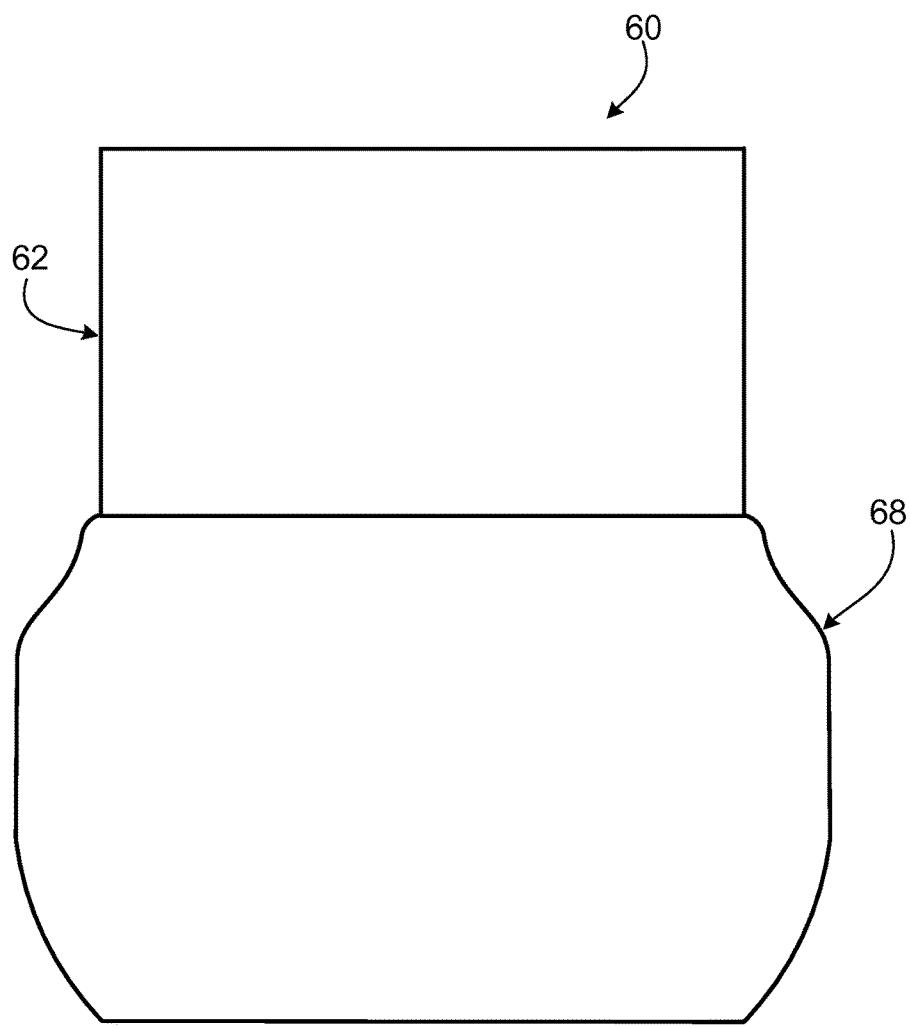
FIG. 9 is a side view of a prosthetic heart valve.
Figure 10:
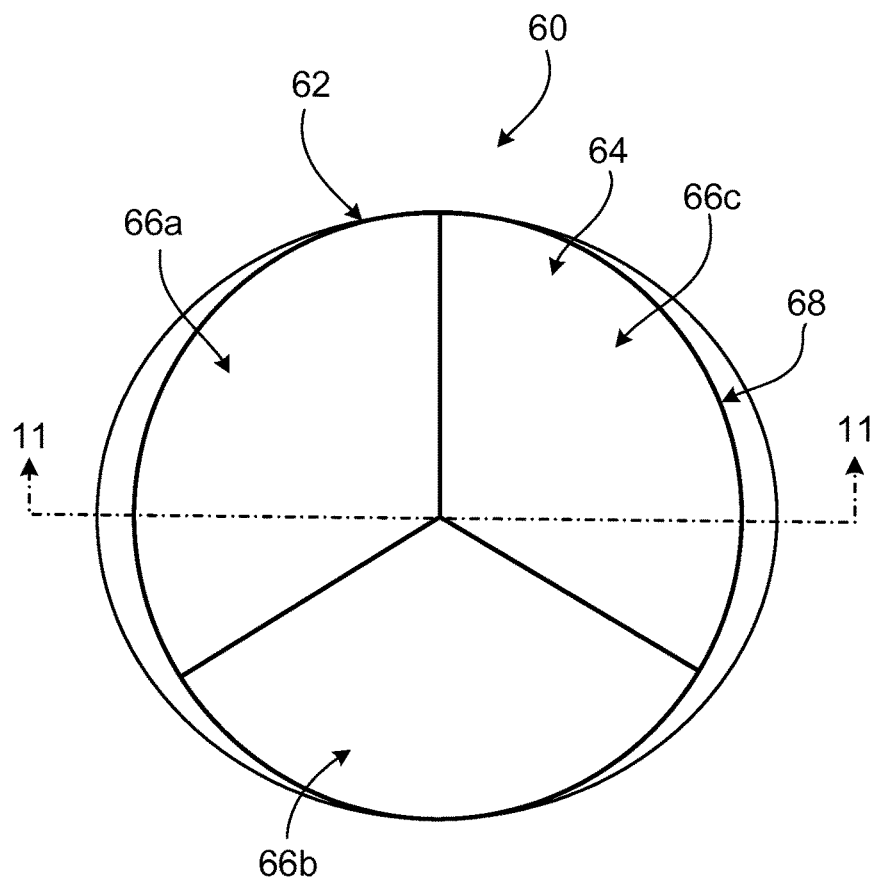
FIG. 10 is a top view of the prosthetic heart valve of FIG. 9.
Figure 11:
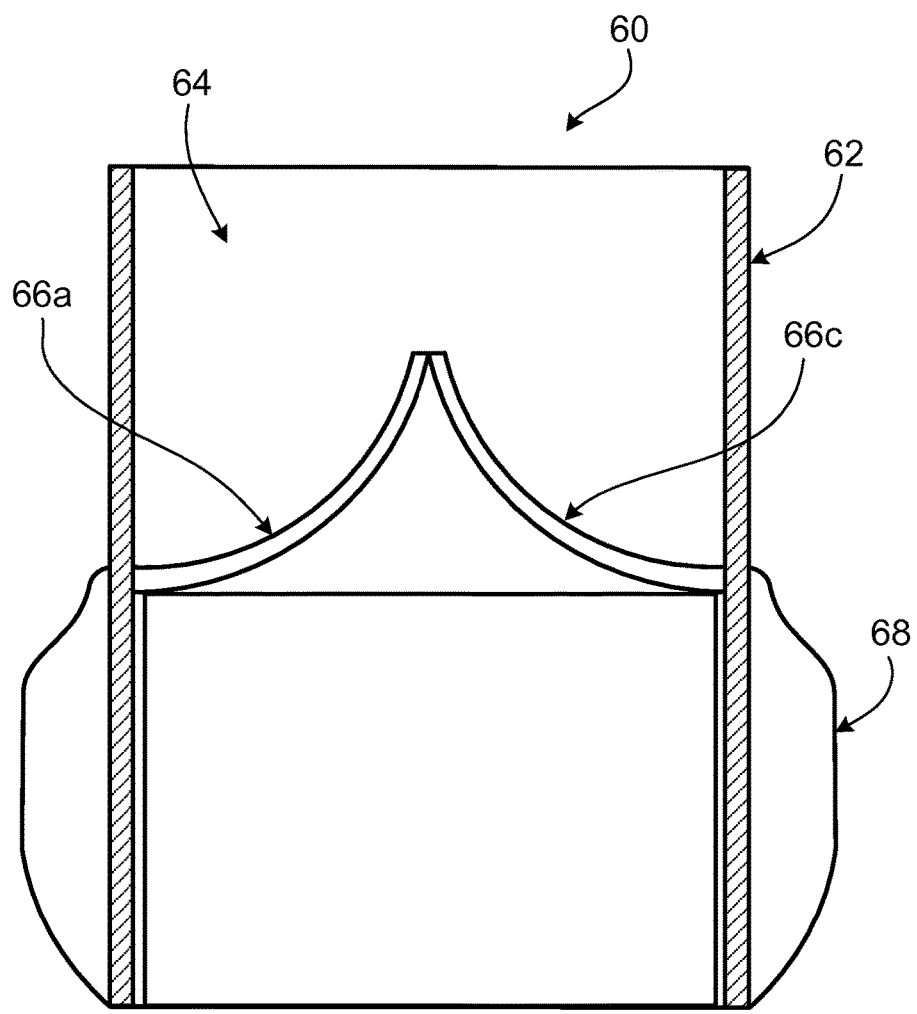
FIG. 11 is a cross-sectional view of the prosthetic valve of FIG. 9 along line 11-11.

As another example, while the prosthetic heart valves have been described as being concentric (e.g., substantially cylindrical), other implementations are additionally or alternatively possible. For example, referring to FIGS. 9-11, a prosthetic heart valve 60 includes a base 62 defining a substantially cylindrical passage 64, plurality of polymeric leaflets 66a,b,c (e.g., similar to polymeric leaflets 14a,b,c in FIGS. 1-3) disposed along the substantially cylindrical passage 64, and a skirt 68 disposed about the base 62. The skirt 68 is eccentrically arranged relative to the substantially cylindrical passage 64. Such an eccentric skirt 68 can fill the void space between the polymeric heart valve 60 and the native valve wall and, for example, reduce the likelihood of paravalvular leakage when the prosthetic heart valve 60 is implanted.

The skirt 68 can include one or more polymers (e.g., the first polymer 26 and/or the second polymer 28 in FIGS. 1-3). In some implementations, the skirt 68 is integral with the base 62. In certain implementations, the skirt 68 is a flap coupled to the base 62 for a lower profile (e.g., during transcatheter delivery) and is movable into position about the base 62 during implantation.

As yet another example, while coating processes have been described as including a cutting step to form edge portions of polymeric leaflets of a prosthetic heart valve, other implementations are additionally or alternatively possible. For example, referring to FIGS. 12A-D, prosthetic heart valves (e.g., prosthetic heart valve 10) can be formed through one or more processes generally including dispending the first solution 26' and the second solution 28' on either side of a wall (e.g., a shim) disposed in a volume defined by the frame 22, reducing or eliminating the need to cut the first and second polymers 26, 28 to form the leaflets 14a,b,c.

Figure 12A:
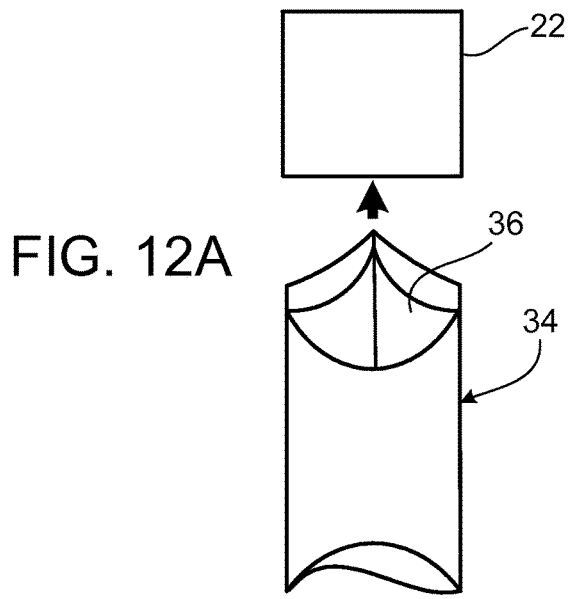
FIGS. 12A-D are schematic illustrations of steps of spray forming in the formation of a prosthetic heart valve.

Referring to FIG. 12A, a mold 70 (e.g., a mandrel) includes a leaflet form 72 and a divider 74 having substantially planar surfaces extending above the leaflet form 72. The divider 74 can be, for example, a shim. As another example, the divider 74 can have variable thickness such that the spacing between the leaflets 14a,b,c (FIGS. 1-3) formed is variable in a radial direction of the with respect to the frame 22.

Figure 12B:
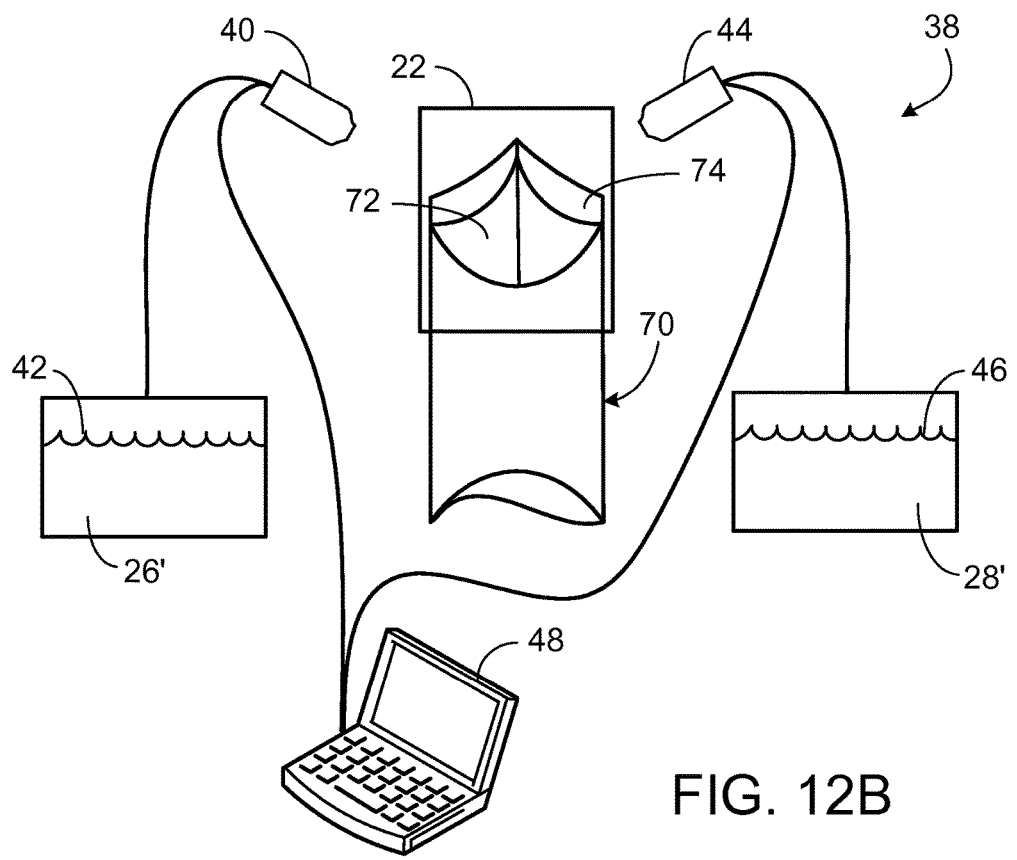

Referring to FIG. 12B, the mold 70 can be positioned in a volume defined by the frame 22 (e.g., a radially expandable stent in an expanded position) such that the leaflet form 72 is at the position at which the polymeric leaflets 14a,b,c (FIGS. 1-3) are to be formed and the divider 74 extends above the leaflet form 72. The first and second solutions 26', 28' are applied by spray system 38 to the leaflet form 72 on either side of the substantially planar surfaces of the divider 74 such that the divider 74 separates the leaflets 14a,b,c (FIGS. 1-3) after the first and second solutions 26', 28' have been applied.

Figure 12C:
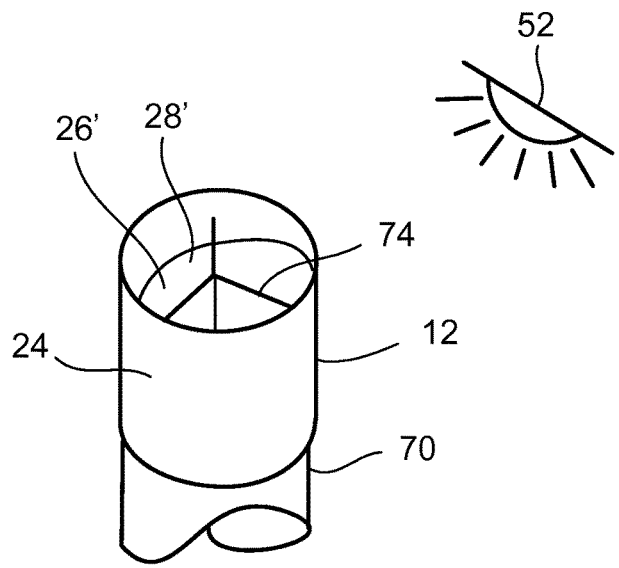

Referring to FIG. 12C, the first and second solutions 26', 28' can be dried in the presence of a heat source 52 in a manner substantially analogous to the drying described above with respect to FIG. 5C. However, it should be appreciated that the divider 74 is disposed between the leaflets 14a,b,c (FIGS. 1-3) while the mold 70 is disposed in a volume defined by the frame 22 (FIG. 12B). Once the first and second solutions 26', 28' are substantially dry, the mold 70, including the divider 74, can be removed from the frame 22.

Figure 12D:
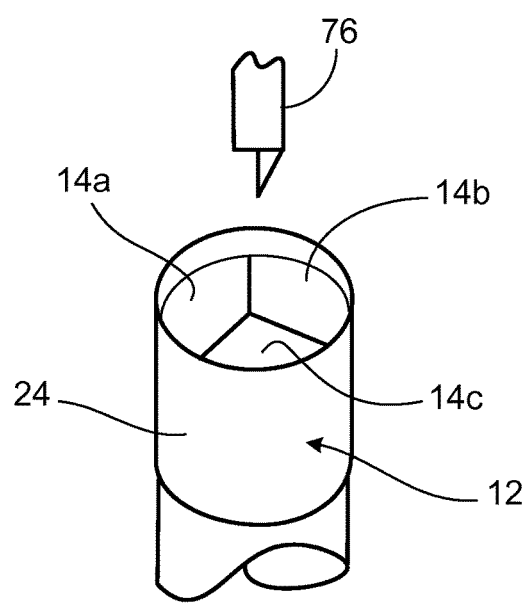

Referring to FIG. 12D, a trimming element 76 can be directed toward the leaflets 14a,b,c to remove excess amounts (e.g., flash) of the first and/or second polymer 26,28 left on either side of the divider 74. The trimming element 76 can include, for example, a blade or a laser.

As still another example, while spray coating processes for forming the prosthetic heart valves have been described as coating the frame and the leaflet form together, other embodiments are additionally or alternatively possible. For example, referring to FIGS. 13A-E, a spray coating can be applied to the frame 22 and the leaflets 14a,b,c can be formed separately.

Figure 13A:
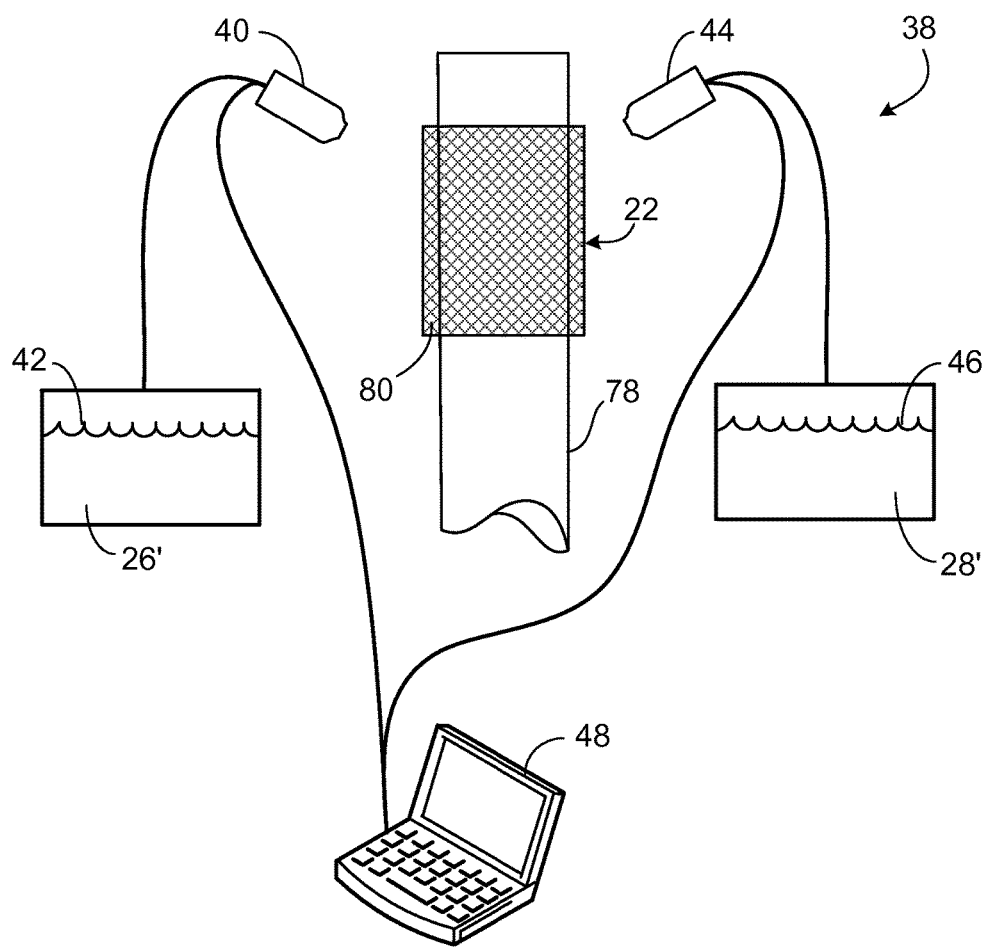
FIGS. 13A-B are schematic illustrations of steps of spray forming in the formation of prosthetic heart valve.

Referring to FIG. 13A, a base mold 78 can be positioned within a volume defined by the frame 22. An outer diameter of the base mold 78 is less than an inner diameter of the frame 22 such that a clearance 80 is defined therebetween. The spray system 38 applies the first solution 26' and/or the second solution 28' to the frame 22 such that the first and/or the second solutions 26', 28' coats one or more surfaces of the frame 22, including filling in the clearance 80, to form the base 12. In some implementations, one or more portions of the frame 22 are masked while the first and/or the second solutions 26', 28' are applied to the frame 22, and the mask is later removed such that the first and/or the second polymer are not deposited on the previously-masked portions of the frame 22. The first and/or second solutions 26', 28' on the frame 22 can be dried (e.g., by exposure to a heat source 52 as described above with respect to FIG. 5C) and the base mold 78 can be removed from the base 12.

Figure 13B:
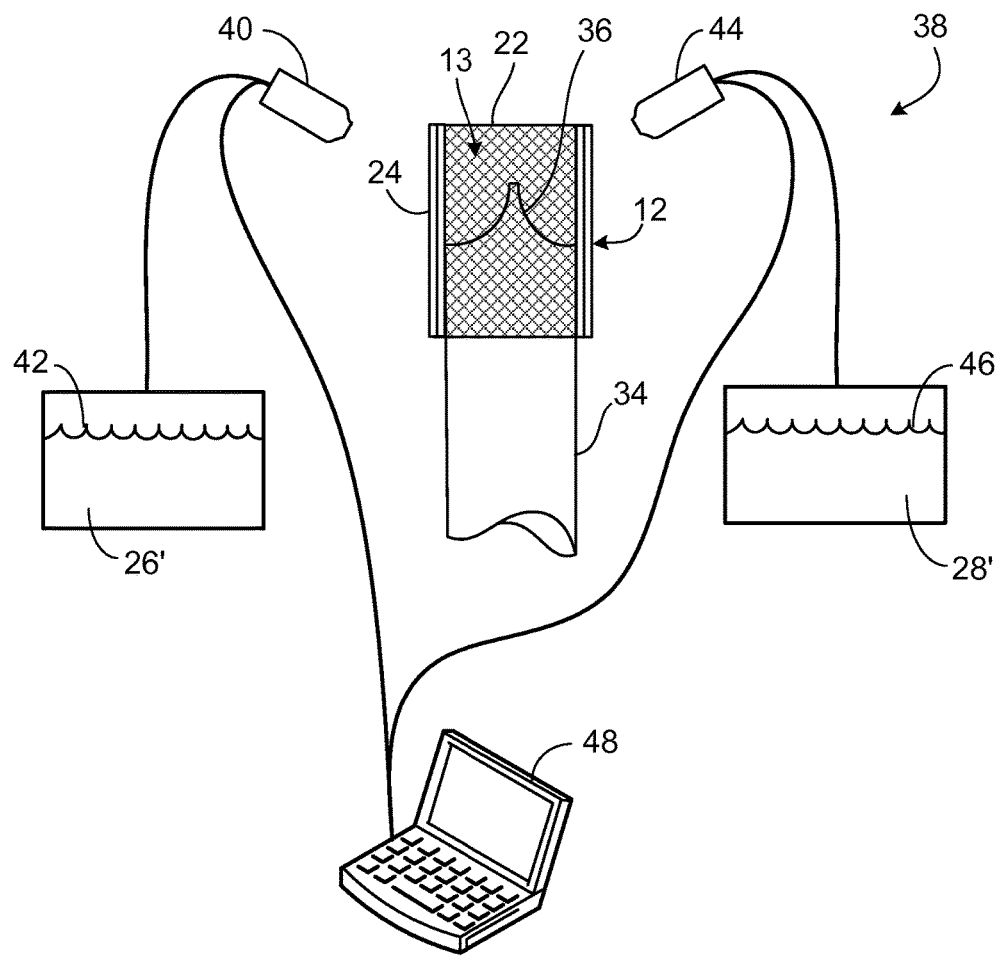

Referring to FIG. 13B, the mold 34 can be positioned along the substantially cylindrical passage 13 defined by the base 12. The first solution 26' and the second solution 28' can be applied (e.g., spray coated) to the leaflet form 36 to form the shape of the leaflets 14a,b,c and couple each root portions 16a,b,c to the base 12 (FIGS. 1-3). The first solution 26' and the second solution 28' can be dried (e.g., by exposure to a heat source 52 as described above with respect to FIG. 5C) and the respective edge portions 18a,b,c of each leaflet 14a,b,c (FIGS. 1-3) can be formed (e.g., through cutting as described above with respect to FIG. 5D).

As yet another example, while the method of forming prosthetic heart valves has been described as including a spray coating process, other processes are additionally or alternatively possible. For example, referring to FIGS. 14A-C, forming prosthetic heart valves can include dip coating at least a portion of a mold into one or more polymer solutions.

Figure 14A:
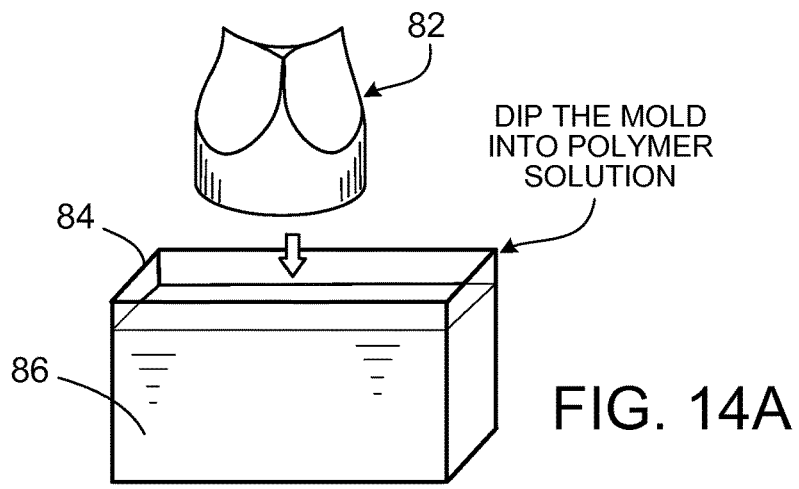
FIGS. 14A-C are schematic illustrations of steps of dip coating in the formation of a prosthetic heart valve.

Referring to FIG. 14A, a form 82 can be dipped into a reservoir 84 containing a polymer solution 86. The form 82 can include a frame (e.g., frame 22) and/or a mold (e.g., mold 34), and the polymer solution 86 can include the first and/or second polymer solutions (26', 28' in FIGS. 5A-5C). The depth and dip rate of movement of the form 82 into the reservoir 84 can be controlled to control the distribution and thickness of the polymer solution 86 on the form 82. Additionally or alternatively, one or more portions of the form 82 can be masked prior to dipping the form 82 into the polymer solution 86 to control the distribution of the polymer solution 86 on the form 82.

Figure 14B:
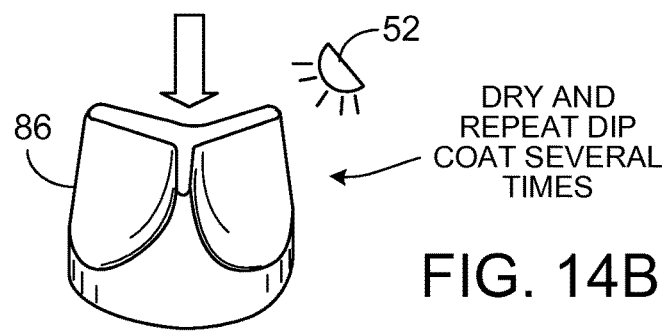

Referring to FIG. 14B, the polymer solution 86 can be dried on the form 82 by exposure to a heat source 52. Once the polymer solution 86 is substantially dried, the form 82 can be dipped in the polymer solution 86 or in another polymer solution having a different polymer and/or a different solvent. The process of drying polymer solutions on the form 82 and dipping the form 82 in a polymer solution can be repeated to achieve a desired distribution and thickness of the first and second polymers 26, 28 along the base 12 and the leaflets 14a,b,c. After a final drying step, the base 12 can be removed from the form 82.

Figure 14C:
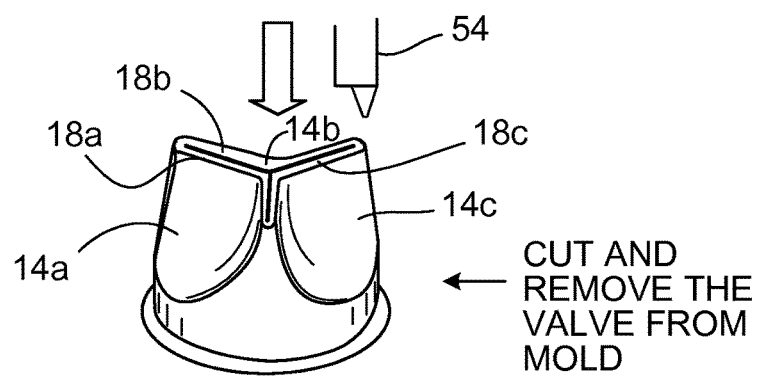

Referring to FIG. 14C, edge portions 18a,b,c of each leaflet 14a,b,c are formed by directing the cutting element 54 toward the leaflets 14a,b,c.

Figure 15A:
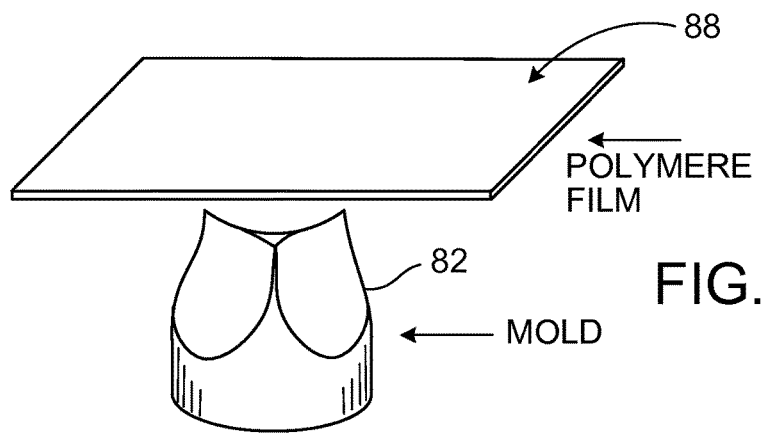
FIGS. 15A-C are schematic illustrations of steps of vacuum forming in the formation of a prosthetic heart valve.
Figure 15B:
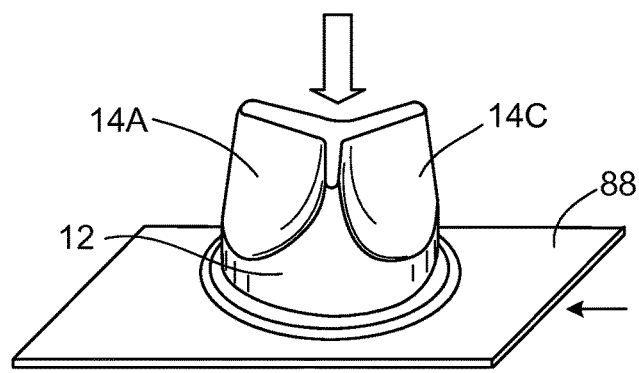
Figure 15C:
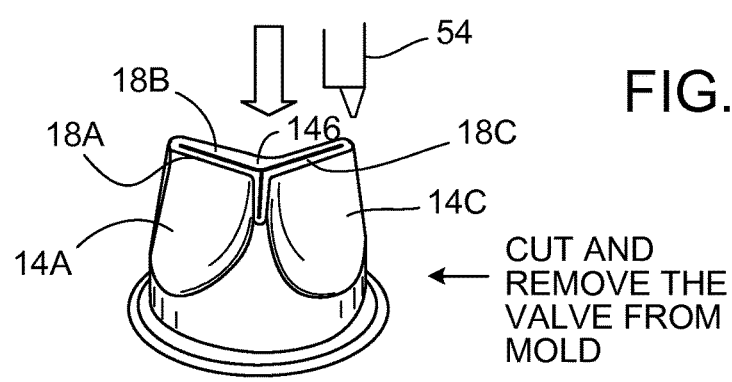

Referring to FIGS. 15A-C, forming prosthetic heart valves can include vacuum forming the first and/or second polymer 26, 28 on the form 82. As compared to spray coating and dip coating, vacuum forming does not require drying the polymers and, thus, can reduce processing time and/or facilitate accurate positioning of the first and/or second polymers 26,28 on the prosthetic heart valve 10.

Referring to FIGS. 15A-B, a film 88 includes the first and/or second polymer 26,28 (FIGS. 1-3). The film 88 is vacuum formed (e.g. through the application of a vacuum pressure) onto the form 82 such that, as shown in FIGS. 1-3 for example, the first and/or second polymer 26, 28 have the desired distribution, thickness, and/or composition gradient along the base 12 and/or the leaflets 14a,b,c. In some implementations, the film 88 is vacuum formed onto a portion of the form 82 to form the base 12. In certain implementations, the film 88 is vacuum formed onto a portion of the form 82 to form the leaflets 14a,b,c.

Referring to FIG. 15C, the cutting element 54 can be directed toward the leaflets 14a,b,c to form the edge portions 18a,b,c, and the form 82 can be removed from the prosthetic heart valve 10.

Figure 16:
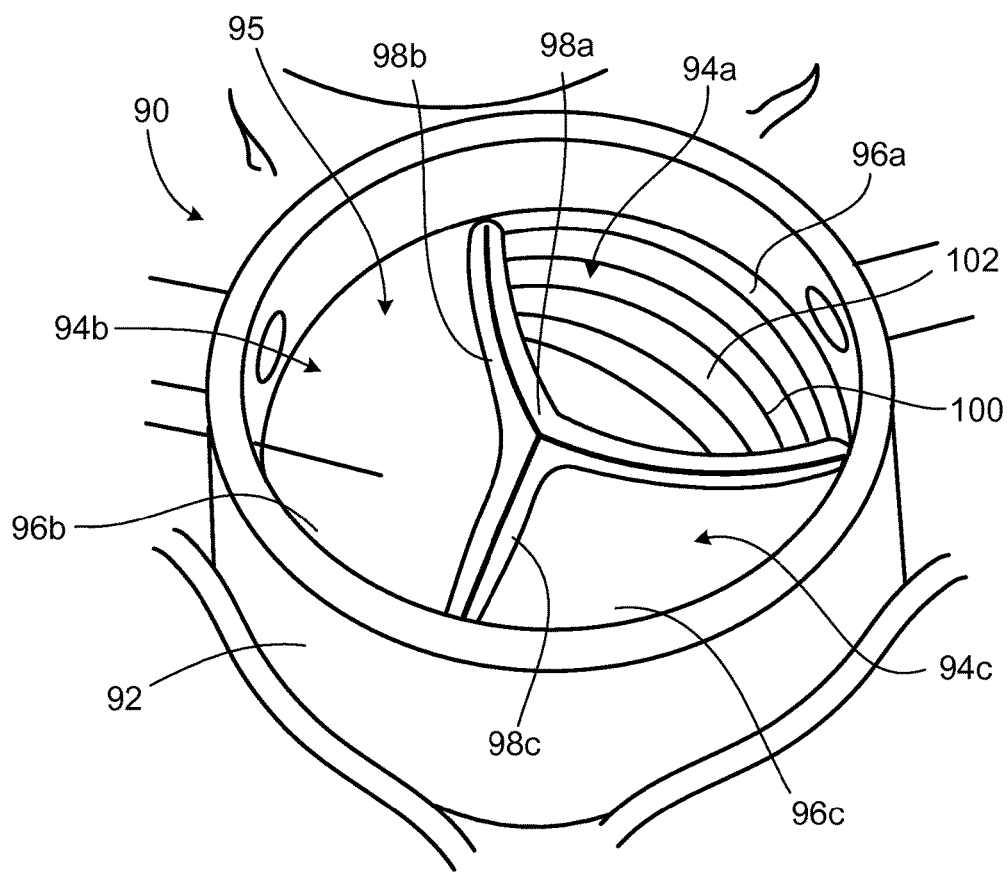
FIG. 16 is a perspective view of a prosthetic heart valve including fiber reinforced leaflets.

As another example, leaflets have been described as including a first and a second polymer having a composition gradient along at least a portion of each leaflet. However, other implementations are additionally or alternatively possible. For example, referring to FIG. 16, a valve 90 includes a base 92 and a plurality of leaflets 94a,b,c disposed in a volume 95 defined by the base 92. Each leaflet 94 a,b,c has a respective root portion 96a,b,c coupled to the base 92 and a respective edge portion 98a,b,c substantially opposite the root portion 96a,b,c and moveable relative to the root portion 96a,b,c to coapt with a respective edge portion 96a,b,c of at least one of the other leaflets 94a,b,c. Each leaflet 94a,b,c includes a plurality of fibers 100 at least partially embedded in a polymer 102. For the sake of clarity of illustration, the fibers 100 are shown only in leaflet 94a. However, it should be appreciated that the fibers 100 are also at least partially embedded in leaflets 94b,c.

As described in further detail below, the fibers 100 can be oriented along the leaflets 94a,b,c to impart desired mechanical properties (e.g., stiffness) to the leaflets 94a,b,c. Additionally, the polymer 102 can be a combination of one or more polymers (e.g., the first and second polymers 26 and 28 of FIGS. 1-3) with a composition gradient of one or more polymers along at least a portion of each leaflet 94a,b,c, for example, to impart further desired mechanical properties to the leaflets 94a,b,c. Fibers 100 and the composition of one or more polymers can be arranged to impart anisotropic mechanical properties in each leaflet 94a,b,c.

The fibers 100 can include one or more of the following: polyester, ultra-high-molecular weight polyethylene, liquid crystalline polymer (LCP) fibers (e.g., Kevlar® available from DuPont Protection Technologies, Richmond, Va., Nomex® available from Dupon Protection Technologies, Richmond, Va., and Vectran® available from the Kuraray America, Inc., Houston, Tex.), NiTi wire mesh, graphene, carbon fiber nanotubes, etc.

The fibers 100 can be at least partially embedded into the polymer 102 with a controlled count and directionality to achieve desired mechanical properties of the leaflets 94a,b,c. For example, each of the fibers 100 can extend in circumferential direction along each respective leaflet 94a,b,c— e.g., a direction substantially perpendicular to a direction extending from the root portion 96a,b,c to the edge portion 98a,b,c of each respective leaflet 94a,b,c. Additionally or alternatively, the fibers 100 can be embedded in each respective leaflet 94a,b,c such that the concentration of fibers 100 decreases in a direction along each leaflet 94a,b,c (e.g., in a direction from the respective root portion 96a,b,c to the respective edge portion 98a,b,c). This can result in each respective leaflet 94a,b,c having one or more anisotropic mechanical properties (e.g., stiffness). In some implementations, a higher concentration of fibers 100 toward the root portion 96a,b,c results in increased stiffness of the respective leaflet 94a,b,c toward the root portion 96a,b,c. In certain implementations, the fibers 100 can be arranged in a cross-hatch pattern. For example, the fibers 100 in a cross-hatch pattern can be more circumferential toward the root portion 96a,b,c of each respective leaflet 94a,b,c.

Figure 17:
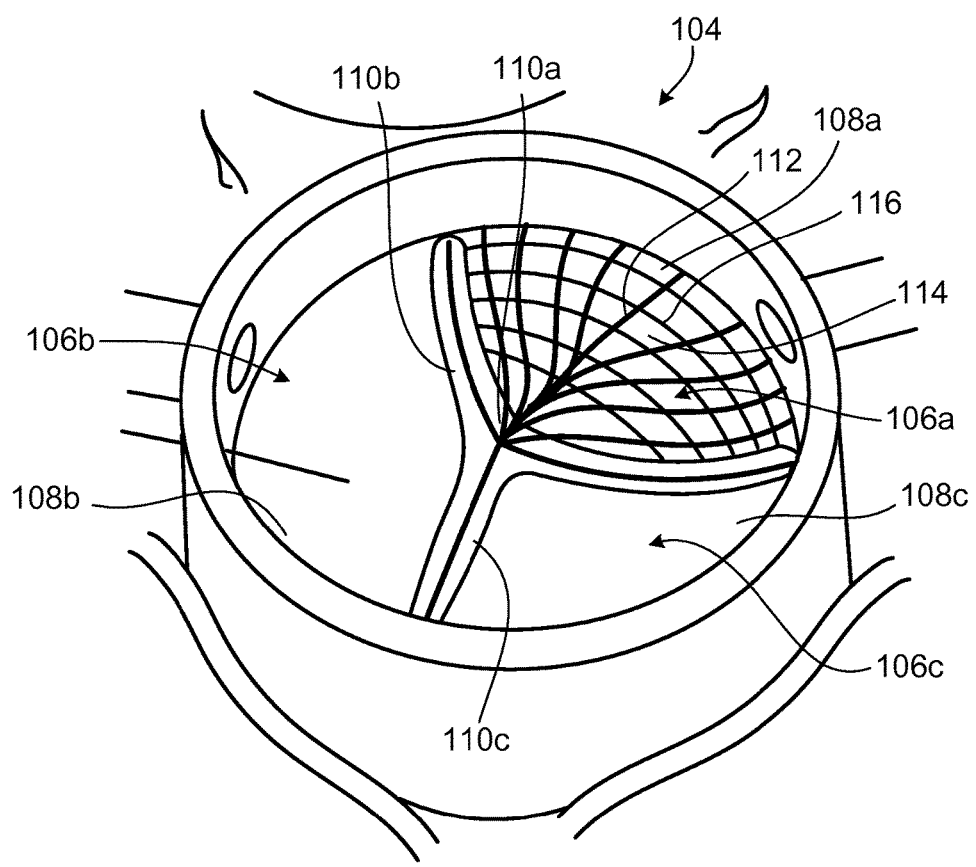
FIG. 17 is a perspective view of a prosthetic heart valve including fiber reinforced leaflets.

As another example, referring to FIG. 17, a valve 104 includes a plurality of leaflets 106a,b,c, each having a root portion 108a,b,c and an edge portion 110a,b,c. Each leaflet 106a,b,c includes a plurality of radial fibers 112 at least partially embedded in a polymer 114 and a plurality of circumferential fibers 116 at least partially embedded in the polymer 114. The polymer 114 can include one or more polymers (e.g., the first polymer 26 and the second polymer 28) having a composition gradient along at least a portion of the leaflets 106a,b,c.

Each of the radial fibers 112 extends in a direction substantially parallel to a direction extending generally from the root portion 108a,b,c to the edge portion 110a,b,c of the respective leaflet 106a,b,c. Each of the circumferential fibers 116 extends in a direction substantially perpendicular to a direction extending generally from the root portion 108a,b,c to the edge portion 110a,b,c of the respective leaflet 106a,b,c. For the sake of clarity of illustration, the radial fibers 112 and the circumferential fibers 116 are shown only in leaflet 106a. However, it should be appreciated that the fibers 112, 116 are also at least partially embedded in leaflets 106b,c.

While the fibers 112,116 are described as having a particular orientation, the fibers 112, 116 can be substantially randomly oriented relative to one another. This can be useful for example, for imparting substantially isotropic mechanical properties to the leaflets 106a,b,c.

Figure 18:
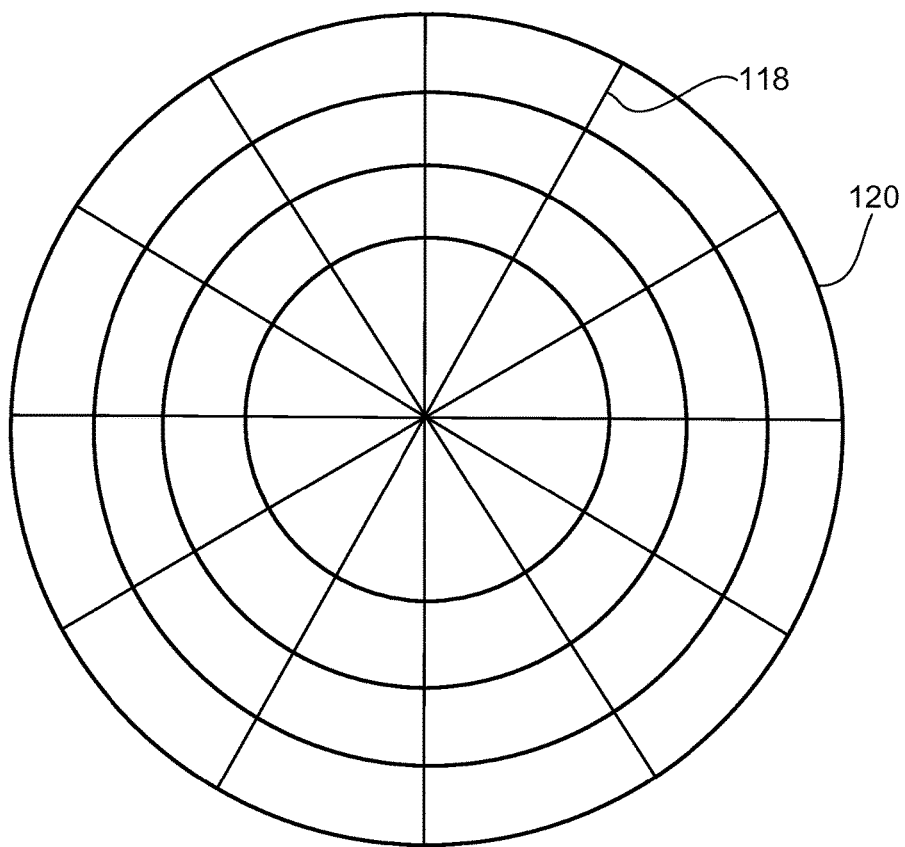
FIG. 18 is a top view of a mold for forming fiber reinforced leaflets.

Referring to FIG. 18, the fibers 112,116 (can be at least partially embedded in the polymer 114 by positioning the fibers 112,116 in grooves 118 defined by a mold 120. The polymer 114 can be formed into the leaflets 106a,b,c (FIG. 17) through one or more of the spray coating and dip coating processes described above.

In some implementations, the fibers 112, 116 are preformed in a film of polymer 114. The polymer 114 can be formed into the leaflets 106a,b,c (FIG. 17) through one or more of the vacuum forming processes described above.
[0001] A number of implementations have been described. Nevertheless, it will be understood that various modifications may be made without departing from the spirit and scope of this disclosure. For example, while implementations have been described as being directed to prosthetic heart valves including a frame, other implementations can be frameless. As another example, while implementations have been described as being directed to prosthetic heart valves including three leaflets, other implementations can include fewer leaflets (e.g., two leaflets) or more leaflets (e.g., four leaflets). As yet another example, while implementations have been described as being directed to prosthetic heart valves, other implementations. Accordingly, other implementations are within the scope of the following claims.

What is claimed is:

1. A prosthetic heart valve comprising:
   a base;
   a plurality of polymeric leaflets, each leaflet having a root portion coupled to the base, each leaflet having an edge portion opposite the root portion and movable relative to the root portion to coapt with a respective edge portion of at least one of the other leaflets of the plurality of leaflets, each leaflet comprising at least two polymers;
   wherein one of the at least two polymers is in the form of a plurality of fibers at least partially embedded in the other polymer and extending from the root portion to the edge portion within each leaflet;
   wherein the fibers are arranged such that a fiber concentration gradient is formed from the root portion to the edge portion within each leaflet such that there is a continuously decreasing concentration of fibers in a direction from the root portion to the edge portion within each leaflet; and
   wherein each leaflet has a uniform thickness.

2. The prosthetic heart valve of claim 1, wherein each leaflet has a stiffness gradient along at least one portion of the leaflet corresponding to the fiber concentration gradient.

3. The prosthetic heart valve of claim 2, wherein each leaflet has the fiber concentration gradient and the stiffness gradient in the direction extending from the root portion to the edge portion.

4. The prosthetic heart valve of claim 2, wherein each leaflet has the fiber concentration gradient and the stiffness gradient in a direction extending along the thickness of the leaflet.

5. The prosthetic heart valve of claim 2, wherein each leaflet has a maximum thickness of 100 μm or less.

6. The prosthetic heart valve of claim 1, wherein at least one of the at least two polymers has hard segments and soft segments.

7. The prosthetic heart valve of claim 6, wherein at least one of the at least two polymers is a block polymer, wherein the soft segments of the block polymer are a copolymer of a first monomer and a second monomer and a comonomer ratio of the first monomer to the second monomer is varied in combination with a hard segment to soft segment ratio, wherein the first monomer is dimethyl siloxane and the second monomer is hexamethylene carbonate.

8. The prosthetic heart valve of claim 1, wherein at least one of the at least two polymers is a polyurethane block polymer and/or a polyurethane urea block polymer.

9. The prosthetic heart valve of claim 1, wherein at least one of the at least two polymers is one or more of the following: polycarbonate urethane; poly(dimethylsiloxane urethane); and poly(isobutylene urethane).

10. The prosthetic heart valve of claim 1, further comprising a skirt disposed about the base, the base defining a concentric passage therethrough, and the skirt eccentrically arranged relative to the concentric passage of the base.

11. The prosthetic heart valve of claim 1, wherein the base comprises one or more of the at least two polymers.

12. The prosthetic heart valve of claim 1, wherein the fibers extend in a direction perpendicular to the direction extending from the root portion to the edge portion of each leaflet.

13. The prosthetic heart valve of claim 1, wherein the fibers are arranged in a cross-hatch pattern.

14. The prosthetic heart valve of claim 1, the fibers including a plurality of radial fibers extending in a direction parallel to the direction extending from the root portion to the edge portion of each leaflet, and a plurality of circumferential fibers extending in a direction perpendicular to the direction extending from the root portion to the edge portion of each leaflet.

15. A prosthetic heart valve comprising:
a base;
a plurality of polymeric leaflets, each leaflet having a root portion coupled to the base, each leaflet having an edge portion opposite the root portion and movable relative to the root portion to coapt with a respective edge portion of at least one of the other leaflets of the plurality of leaflets, each leaflet comprising at least two polymers;
wherein one of the at least two polymers is in the form of a plurality of fibers at least partially embedded in the other polymer of each leaflet, wherein the plurality of fibers are arranged along an axis from the root portion to the edge portion of each leaflet, and
wherein the plurality of fibers arranged along the axis varies such that the number of fibers decreases continuously along the axis in a direction from the root portion to the edge portion of each leaflet to form a fiber concentration gradient; and
wherein each leaflet has a uniform thickness.

16. The prosthetic heart valve of claim 15, wherein the fiber concentration gradient along the axis in the direction from the root portion to the edge portion of each leaflet imparts one or more anisotropic mechanical properties to the leaflets.

* * * * *